(12) United States Patent
Eibl et al.

(10) Patent No.: US 7,193,131 B2
(45) Date of Patent: Mar. 20, 2007

(54) PROCESSES AND VECTORS FOR PLASTID TRANSFORMATION OF HIGHER PLANTS

(75) Inventors: Christian Eibl, Ismaning (DE); Fong-Chin Huang, Munich (DE); Sebastian Klaus, Graefelfing (DE); Stefan Mühlbauer, Freising (DE); Stefan Herz, Munich (DE); Hans-Ulrich Koop, Munich (DE)

(73) Assignee: Icon Genetics AG, Munich (DE)

( * ) Notice: Subject to any disclaimer, the term of this patent is extended or adjusted under 35 U.S.C. 154(b) by 98 days.

(21) Appl. No.: 10/466,221

(22) PCT Filed: Jan. 18, 2002

(86) PCT No.: PCT/EP02/00481

§ 371 (c)(1),
(2), (4) Date: Dec. 29, 2003

(87) PCT Pub. No.: WO02/057466

PCT Pub. Date: Jul. 25, 2002

(65) Prior Publication Data

US 2004/0083499 A1    Apr. 29, 2004

(30) Foreign Application Priority Data

Jan. 19, 2001    (DE)    ............................... 101 02 389

(51) Int. Cl.
    *C12N 15/82*    (2006.01)
(52) U.S. Cl. ...................................... 800/278
(58) Field of Classification Search ................ None
    See application file for complete search history.

(56) References Cited

U.S. PATENT DOCUMENTS

| | | |
|---|---|---|
| 5,139,812 A | 8/1992 | Lebacq |
| 5,474,925 A | 12/1995 | Maliyakal et al. |
| 5,576,198 A | 11/1996 | McBride et al. |
| 5,627,059 A | 5/1997 | Capecchi et al. |
| 5,670,623 A | 9/1997 | Shoseyov et al. |
| 5,723,765 A | 3/1998 | Oliver et al. |
| 5,877,402 A | 3/1999 | Maliga et al. |
| 6,100,448 A | 8/2000 | Thompson et al. |
| 6,147,278 A | 11/2000 | Rogers et al. |
| 6,174,700 B1 | 1/2001 | Haynes et al. |
| 6,300,545 B1 | 10/2001 | Baszczynski et al. |
| 6,331,416 B1 | 12/2001 | Shani et al. |
| 6,331,661 B1 | 12/2001 | Baszczynski et al. |
| 6,781,033 B2 | 8/2004 | Staub et al. |
| 2004/0055037 A1 | 3/2004 | Gleba et al. |
| 2004/0088764 A1 | 5/2004 | Gleba et al. |
| 2004/0137631 A1 | 7/2004 | Herz et al. |
| 2004/0191788 A1 | 9/2004 | Gleba et al. |
| 2004/0221330 A1 | 11/2004 | Klimyuck et al. |
| 2004/0244073 A1 | 12/2004 | Klimyuck et al. |
| 2004/0255347 A1 | 12/2004 | Klimyuck et al. |
| 2005/0014510 A1 | 1/2005 | Atabekov et al. |
| 2005/0015829 A1 | 1/2005 | Koop et al. |
| 2005/0015830 A1 | 1/2005 | Dorokhov et al. |
| 2005/0059004 A1 | 3/2005 | Atabekov et al. |
| 2005/0066384 A1 | 3/2005 | Klimyuck et al. |
| 2005/0091706 A1 | 4/2005 | Klimyuck et al. |

FOREIGN PATENT DOCUMENTS

| | | |
|---|---|---|
| EP | 0270 248 | 6/1988 |
| EP | 1 045 037 | 10/2000 |
| WO | 87/00551 | 1/1987 |
| WO | 94/16089 | 7/1994 |
| WO | 95/34668 | 12/1995 |
| WO | 96/17954 | 6/1996 |
| WO | 98/09505 | 3/1998 |
| WO | 98/44097 | 10/1998 |
| WO | 98/54342 | 12/1998 |
| WO | 99/25821 | 5/1999 |
| WO | 99/25855 | 5/1999 |
| WO | 99/36516 | 7/1999 |
| WO | 01/11020 | 2/2000 |
| WO | 00/17365 | 3/2000 |
| WO | 00/20611 | 4/2000 |
| WO | WO00/32799 | 6/2000 |

(Continued)

OTHER PUBLICATIONS

Allison et al., "Deletion of rpoB Reveals a Second Distinct Transcription System in Plastids of Higher Plants," *The EMBO Journal*, 15:11 2802-2809 (1996).
Bogorad, Lawrence, "Engineering Chloroplasts: an Alternative Site for Foreign Genes, Proteins, Reactions and Products," *TIBTECH*, 18:257-263 (Jun. 2000).
Boynton et al., "Chloroplast Transformation in *Chlamydomonas* with High Velocity Microprojectiles," *Science*, 240:1534-1538 (1988).
Daniell, Henry, "New Tools for Chloroplast Genetic Engineering," *Nature Biotechnology*, 17:855-856 (Sep. 1999).
De Santis-Maciossek et al., "Targeted Disruption of the Plastid RNA Polymerase Genes *rpoA*, *B* and *C1*: Molecular Biology, Biochemistry and Ultrastructure," *The Plant Journal*, 18(5):477-489 (1999).
Fischer et al., "Selectable Marker Recycling in the Chloroplast," *Mol. Gen. Genet.*, 251:373-380 (1996).

(Continued)

*Primary Examiner*—Anne Kubelik
(74) *Attorney, Agent, or Firm*—Myers Bigel Sibley & Sajovec, PA

(57) ABSTRACT

A process for producing multicellular plants, plant organs or plant tissues transformed on their plastome by the following steps is provided: (a) altering or disrupting the function of a gene in a plastid genome for producing a selectable or recognizable phenotype; (b) separating or selecting plants or cells having plastids expressing said phenotype; (c) transforming said plastid genome of said separated or selected plant, plant organ or plant tissue with at least one transformation vector having a restoring sequence capable of restoring said function; and (d) separating or selecting said transformed plant, plant organ or plant tissue having plastids expressing said restored function.

27 Claims, 8 Drawing Sheets

FOREIGN PATENT DOCUMENTS

Figure 1:
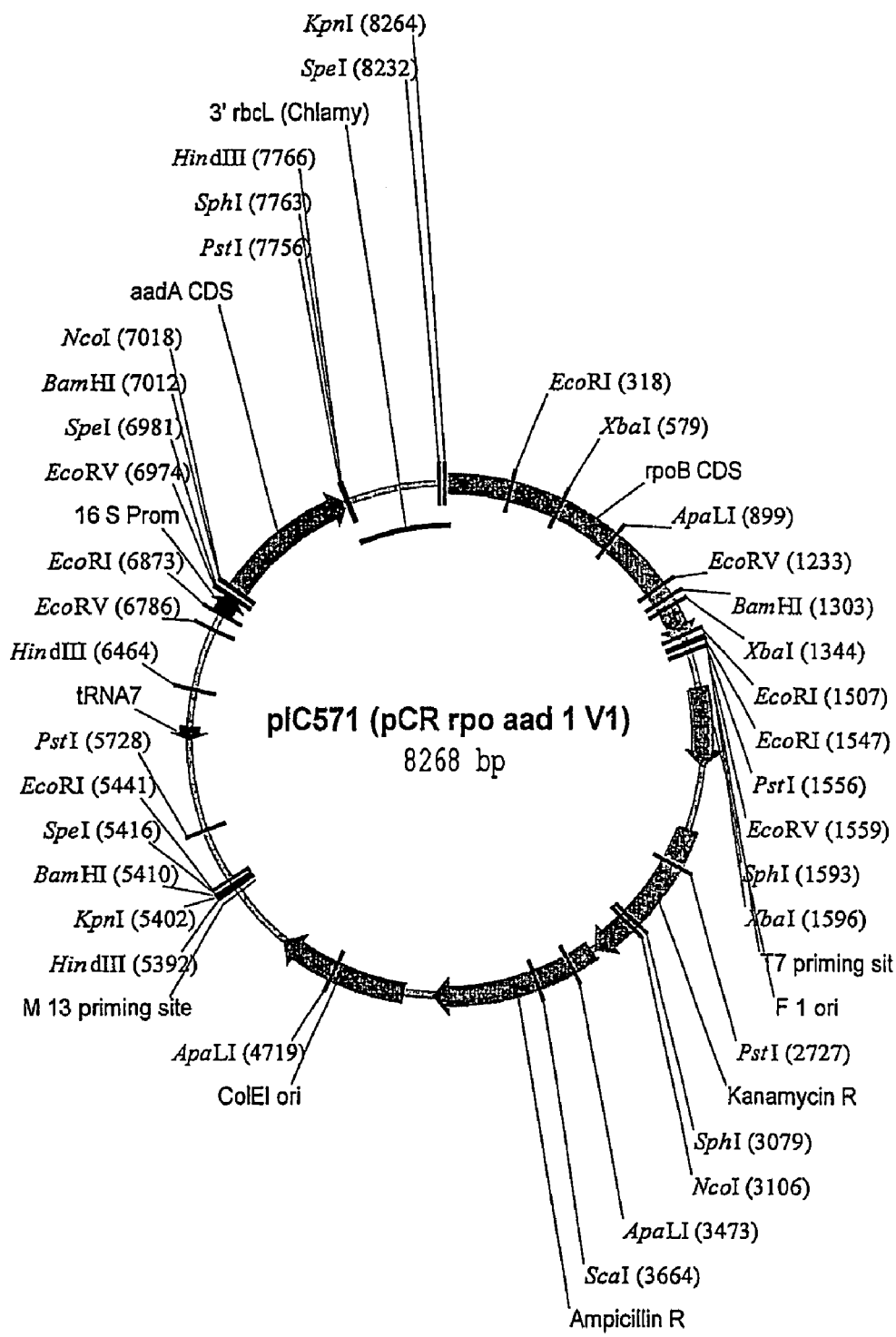

| | | |
|---|---|---|
| WO | 00/68391 | 11/2000 |
| WO | 00/68431 | 11/2000 |
| WO | 00/70019 | 11/2000 |
| WO | 00/77174 | 12/2000 |
| WO | 00/77175 | 12/2000 |
| WO | 00/78985 | 12/2000 |
| WO | 01/59138 | 8/2001 |
| WO | 01/81600 | 11/2001 |
| WO | 02/12522 | 2/2002 |
| WO | 02/29068 | 4/2002 |
| WO | 02/46438 | 6/2002 |
| WO | 02/46440 | 6/2002 |
| WO | 02/055651 | 7/2002 |
| WO | 02/057466 | 7/2002 |
| WO | 02/068664 | 9/2002 |
| WO | 02/077246 | 10/2002 |
| WO | 02/079481 | 10/2002 |
| WO | 02/088369 | 11/2002 |
| WO | 02/101060 | 12/2002 |
| WO | 03/001900 | 1/2003 |
| WO | 03/004658 | 1/2003 |
| WO | 03/020927 | 3/2003 |
| WO | 03/020928 | 3/2003 |
| WO | 03/020938 | 3/2003 |

OTHER PUBLICATIONS

Heifetz, Peter B., "Genetic Engineering of the Chloroplast," *Biochimie*, 82:655-666 (2000).

Kofer et al., "PEG-Mediated Plastid Transformation in Higher Plants," *In Vitro Cell. Dev. Biol.- Plant*, 31:303-309 (1998).

Monde et al., "Post-Transcriptional Defects in Tobacco Chloroplast Mutants Lacking the Cytochrome $b_6/f$Complex," *The Plant Journal*, 21(1):61-72 (2000).

Ruf et al., "Targeted Inactivation of a Tobacco Intron-Containing Open Reading Frame Reveals a Novel Chloroplast-Encoded Photosystem I-Related Gene," *The Journal of Cell Biology*, 139(1):95-102 (Oct. 6, 1997).

Serino et al., "RNA Polymerase Subunits Encoded by the Plastid *rpo* Genes are Not Shared with the Nucleus-Encoded Plastid Enzyme," *Plant Physiol.*, 117:1165-1170 (1998).

Suzuki et al., "Engineering of the *rpl23* Gene Cluster to Replace the Plastid RNA Polymerase α Subunit with the *Escherichia coli* Homologue," *Curr. Genet.*, 38:218-225 (2000).

International Search Report corresponding to PCT/EP01/15034; Date of Mailing: Jun. 19, 2002.

Albert et al. (1995) "Site-specific integration of DNA into wild-type and mutant lox sites placed in the plant genome" The Plant Journal 7:649-659.

Altschul et al. "Basic Local Alignment Search Tool," J. Mol. Biol., 215:403-410 (1990).

Anandalakshmi et al. (1998) "A viral suppressor of gene silencing in plants" Proc. Natl. Acad. Sci. U.S.A. 95:13079-13084.

Anandalakshmi et al. (2000) "A calmodulin-related protein that suppresses posttranscriptional gene silencing in plants" Science 290:142-144.

Arnold et al. "Allelic Ladder, D18S51 Allele 8" EBI Database accession No. AAX01351 (Apr. 14, 1999) Abstract.

Bagwell, BC "Poly-dA 50mer Probe Target Sequence" EBI Database accession No. AAQ66922 (Jan. 24, 1995) Abstract.

Bateman et al. (2000) "Tools for chloroplast transformation in Chlamydomonas: expression vectors and a new dominant selectable marker" Mol. Gen. Genet. 263:401-410.

Bergamini et al. "Picornavirus IRESes and the Poly(A) tail Jointly Promote Cap-Independent Translation in a Mammalian Cell-free System," RNA, 6:1781-1790 (2000).

Bouchez et al. (1993) "A binary vector based on Basta resistance for in planta transformation of *Arabidopsis thaliana*" C. R. Acad. Sci. Paris, Science de la vie 316:1188-1193.

Carpin et al. (2001) "Identification of a Ca2+-Pectate Binding Site on an Apoplastic Peroxidase" The Plant Cell 13:511-520.

Chappell et al. "A 9-nt Segment of Cellular mRNA Can Function as an Internal Ribosome Entry Site (IRES) and When Present In Linked Multiple Copies Greatly Enhances IRES Activity," PNAS, 97(4):1536-1541 (Feb. 14, 2000).

Clelland et al. (1999) "Hiding Messages in DNA Microdots," Nature 399:533-534.

Coutts et al. "Development of Geminivirus-based Gene Vectors for Dicotyledonous Plants" Australian Journal of Plant Physiology 17:365-375 (1990).

Dale et al. "Intra- and intermolecular site-specific recombination in plant cells mediated by bacteriophage P1 recombinase" Gene 91:79-85 (1990).

Dale et al. "Mutations in the CRE/LOX Recombination Site Enhance the Stability of Recombination Products: Applications for Gene Targeting in Plants" Journal of Cellular Biochemistry 50 (S16F):206 (1992).

Domingo et al. (1999) "Identification of a novel peptide motif that mediates cross-linking of proteins to cell walls" The Plant Journal 20:563-570.

Dorokhov et al. "Polypurine (A)-Rich Sequences Promote Cross-Kingdom Conservation of Internal Ribosome Entry" PNAS 99(8):5301-5306 (Apr. 16, 2002).

Drescher et al., "The Two Largest Chloroplast Genome-Encoded Open Reading Frames of Higher Plants are Essential Genes," The Plant Journal, 22(2):97-104 (2000).

El-Sheekh, M.M. (2000) "Stable Chloroplast Transformation in *Chlamydomonas reinhardtii* using Microprojectiie Bombardment" Folia Microbiol. 45(6) 496-504.

Gatz et al. (1991) "Regulation of a modified CaMV 35S promoter by the Tn10-encoded Tet repressor in transgenic tobacco" Mol. Gen. Genet. 227:229-237.

Hager et al., "Enslaved Bacteria as New Hope for Plant Biotechnologists," Appl. Microbiol. Biotechnol., 54:302-310 (2000).

Hoff et al. (2001) "A recombinase-mediated transcriptional induction system in transgenic plants" Plant Mol. Biol. 45:41-49.

Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).

Houdebine et al. "Internal Ribosome Entry Sites (IREs): Reality and Use" Transgenic Research, 8:157-177 (1999).

Iamtham et al. (2000) "Removal of antibiotic resistance genes from transgenic tobacco plastids" Nature Biotechnology 18:1172-1176.

Ivanov et al. "A Tobamovirus Genome That Contains an Internal Ribosome Entry Site Functional In Vitro," Virology, 232:32-43 (1997).

Joen et al. (2000) "T-DNA insertional mutagenesis for functional genomics in rice" Plant J. 22:561-570.

Koshinsky et al. (2000) "Cre-lox site-specific recombination between Arabidopsis and tobacco chromosomes" The Plant Journal 23:715-722.

Kozak, "Initiation of Translation in Prokaryotes and Eukaryotes" Gene 234:187-208 (1999).

Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed immobilization of recombinant staphylococci on cotton fibers by functional display of a fungal cellulose-binding domain" FEMS Microbiology Letters 195:197-204.

Lopez de Quinto et al. "Parameters Influencing Translational Efficiency in Aphthovirus IRES-Based Bicistronic Expression Vectors" Gene 217:51-56 (1998).

Martinez-Salas, Encarnacion. "Internal Ribosome Entry Site Biology and Its Use In Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts" Molec. Gen. Genet. 135:277-294.

Michael et al. (1999) "Efficient gene-specific expression of Cre recombinase in the mouse embryo by targeted insertion of a novel IRES-Cre cassette into endogenous loci" Mech. Dev. 85:35-47.

Mizuguchi et al. (2000) "IRES-Dependent Second Gene Expression Is Significantly Lower Than Cap-Dependent First Gene Expression in a Bicistronic Vector" Mol Ther. 1:376-382.

Mountford et al. (1995) "Internal ribosome entry sites and dicistronic RNAs in mammalian transgenesis" Trends Genet. 11:179-184.

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85: 2444-2448 (Apr. 1988).

Peterson-Burch et al. "Retroviruses in plants?" Trends in Genetics 16:151-152 (2000).

Porta et al. "Use of Viral Replicons for the Expression of Genes in Plants" Molecular Biotechnology 5:209-221 (1996).

Preiss et al. "Dual Function of the Messenger RNA Cap Structure In Poly(A)-tail-promoted Translation in Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat × Tripsacum Crosses" Crop Science 33:973-976.

Schreuder et al. (1993) "Targeting of a Heterologous Protein to the Cell Wall of *Saccharomyces cerevisiae*" Yeast 9:399-409.

Shepard et al. (1983) "Genetic Transfer in Plants Through Interspecific Protoplast Fusion" Science 219:683-688.

Stanley, J. "Geminiviruses: plants viral vectors" Current Opinion in Genetics and Development 3:91-96 (1993).

Staub et al. (1994) "Extrachromosomal elements in tobacco plastids" Proc. Natl. Acad. Sci. 91:7468-7472.

Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in *Chlamydomonas chloroplasts*" Plant J. 11:635-648.

Toth et al. (2001) "A novel strategy for the expression of foreign genes from plant virus vectors" FEBS Lett. 489:215-219.

Ueda et al. (2000) "Genetic immobilization of proteins on the yeast cell surface" Biotechnology Advances 18:121-140.

Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of Agrobacterium T-DNA in *Arabidopsis thaliana* by transient expression of cre" Plant Molecular Biology 38:393-406 (1998).

Urwin et al. (2000) "Functional characterization of the EMCV IRES in plants" Plant J. 24:583-589.

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

Hagemann et al. "Extranuclear Inheritance: Plastid Genetics" *Progress in Botany*, vol. 55, 260-275 (1994).

Klaus et al. "Generation of Marker Free Plastid Transformants Using a Transiently Cointegrated Selection Gene" *Nature Biotechnology* 22: 225-229 (2004).

Ruf et al. "Stable Genetic Transformation of Tomato Plastids and Expression of a Foreign Protein in Fruit" *Nature Biotechnology* 19: 870-875 (2001).

Shimada et al. "Fine Structural Features of the Chloroplast Genome: Comparison of the Sequenced Chloroplast Genomes" *Nucleic Acids Research* 19: 983-995 (1991).

Shinozaki et al. "The Complete Nucleotide Sequence of the Tobacco Chloroplast Genome: Its Gene Organization and Expression" *The EMBO Journal* 5: 2043-2049 (1986).

Sidorov et al. "Stable Chloroplast Transformation in Potato: Use of Green Fluorescent Protein as a Plastid Marker" *The Plant Journal* 19: 209-216 (1999).

Mühlbauer et al. "Functional analysis of plastid DNA replication origins in tobacco by targeted inactivation" *The Plant Journal*, 23:175-184 (2002).

SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
aagatgaacc tgttcccatg                                               20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
cacttcttcc ccacactacg                                               20

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
tgctggccgt acatttgtac g                                             21

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
cactacattt cgctcatcgc c                                             21

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
atttgtagta gaaggtaatt gc                                            22

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ttagtaacaa gcaaaccttg                                               20

<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
taattactga atcgcttccc a                                      21

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
tactattatt tgattagatc                                        20

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
taattactga atcgcttccc a                                      21

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
ttagtaacaa gcaaaccttg                                        20

<210> SEQ ID NO 11
<211> LENGTH: 44
<212> TYPE: DNA
<213> ORGANISM: Artificial Sequence
<220> FEATURE:
<223> OTHER INFORMATION: PCR primer

<400> SEQUENCE: 11
atcactagtt gtagggaggg atccatggtt cgagagaaag taac              44

<210> SEQ ID NO 12
<211> LENGTH: 23
<212> TYPE: DNA
<213> ORGANISM: Artificial Sequence
<220> FEATURE:
<223> OTHER INFORMATION: PCR primer

<400> SEQUENCE: 12
gaagtttctt tctttgctac agc                                    23

<210> SEQ ID NO 13
<211> LENGTH: 22
<212> TYPE: DNA
<213> ORGANISM: Artificial Sequence
<220> FEATURE:
<223> OTHER INFORMATION: PCR primer

<400> SEQUENCE: 13
gaattaccaa accatttgac cc                                          22

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
cactacattt cgctcatcgc c                                           21

<210> SEQ ID NO 15
<211> LENGTH: 21
<212> TYPE: DNA
<213> ORGANISM: Artificial Sequence
<220> FEATURE:
<223> OTHER INFORMATION: PCR primer

<400> SEQUENCE: 15
gactatagtt aatggatact c                                           21

<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
tgctcaagac tttagtggat c                                           21

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
cattggaact gctatgtagg c                                           21

<210> SEQ ID NO 18
<211> LENGTH: 21
<212> TYPE: DNA
<213> ORGANISM: Artificial Sequence
<220> FEATURE:
<223> OTHER INFORMATION: PCR primer

<400> SEQUENCE: 18 gtgttttct cctcgtaaga c                                            21

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
ccgttatgta cacaaaattg                                             20

```
<210> SEQ ID NO 20
<211> LENGTH: 30
<212> TYPE: DNA
<213> ORGANISM: Artificial Sequence
<220> FEATURE:
<223> OTHER INFORMATION: PCR primer

<400> SEQUENCE: 20
ctagctagct tatttgtata gttcatccat                                    30

<210> SEQ ID NO 21
<211> LENGTH: 30
<212> TYPE: DNA
<213> ORGANISM: Artificial Sequence
<220> FEATURE:
<223> OTHER INFORMATION: PCR primer

<400> SEQUENCE: 21
tcccccgggg ccgtcgttca atgagaatgg                                    30

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
gtagcaatcc attctagaat                                               20

<210> SEQ ID NO 23
<211> LENGTH: 38
<212> TYPE: DNA
<213> ORGANISM: Artificial Sequence
<220> FEATURE:
<223> OTHER INFORMATION: PCR primer

<400> SEQUENCE: 23
ggaattccat atggtataaa actcatgtgt gtaagaaa                            38

<210> SEQ ID NO 24
<211> LENGTH: 31
<212> TYPE: DNA
<213> ORGANISM: Artificial Sequence
<220> FEATURE:
<223> OTHER INFORMATION: PCR primer

<400> SEQUENCE: 24
tcccccgggg gtccaatcat tgatcgcgaa a                                  31

<210> SEQ ID NO 25
<211> LENGTH: 36
<212> TYPE: DNA
<213> ORGANISM: Artificial Sequence
<220> FEATURE:
<223> OTHER INFORMATION: PCR primer

<400> SEQUENCE: 25
ttccccgggt tctaaataga aagaaagtca aatttg                             36

<210> SEQ ID NO 26
<211> LENGTH: 33
<212> TYPE: DNA
<213> ORGANISM: Artificial Sequence
<220> FEATURE:
<223> OTHER INFORMATION: PCR primer
```

```
<400> SEQUENCE: 26
catgcatgcg aatgaataag attctcttag ctc                              33

<210> SEQ ID NO 27
<211> LENGTH: 35
<212> TYPE: DNA
<213> ORGANISM: Artificial Sequence
<220> FEATURE:
<223> OTHER INFORMATION: PCR primer

<400> SEQUENCE: 27
tcccccgggt agaaaactat tgatacgtct tatgg                            35

<210> SEQ ID NO 28
<211> LENGTH: 25
<212> TYPE: DNA
<213> ORGANISM: Artificial Sequence
<220> FEATURE:
<223> OTHER INFORMATION: PCR primer

<400> SEQUENCE: 28
aaaatagatt cattagtccg atacc                                       25

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
tcacaccgat accatcagcg                                             20

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
attgtttgcc tccctgctgc                                             20

<210> SEQ ID NO 31
<211> LENGTH: 22
<212> TYPE: DNA
<213> ORGANISM: Artificial Sequence
<220> FEATURE:
<223> OTHER INFORMATION: PCR primer

<400> SEQUENCE: 31
aatcgtaacc agtctctact gg                                          22

<210> SEQ ID NO 32
<211> LENGTH: 21
<212> TYPE: DNA
<213> ORGANISM: Artificial Sequence
<220> FEATURE:
<223> OTHER INFORMATION: PCR primer

<400> SEQUENCE: 32
cggaaagaga gggattctaa c                                           21
```

-continued

```
<210> SEQ ID NO 33
<211> LENGTH: 21
<212> TYPE: DNA
<213> ORGANISM: Artificial Sequence
<220> FEATURE:
<223> OTHER INFORMATION: PCR primer

<400> SEQUENCE: 33
gaagtttctt tctttgctac a                                               21

<210> SEQ ID NO 34
<211> LENGTH: 21
<212> TYPE: DNA
<213> ORGANISM: Artificial Sequence
<220> FEATURE:
<223> OTHER INFORMATION: PCR primer

<400> SEQUENCE: 34
tacgcttttt gaaggtgaag t                                               21

<210> SEQ ID NO 35
<211> LENGTH: 44
<212> TYPE: DNA
<213> ORGANISM: Artificial Sequence
<220> FEATURE:
<223> OTHER INFORMATION: PCR primer

<400> SEQUENCE: 35
atcactagtt gtagggaggg atccatgcct agatcacgga taaa                      44

<210> SEQ ID NO 36
<211> LENGTH: 20
<212> TYPE: DNA
<213> ORGANISM: Artificial Sequence
<220> FEATURE:
<223> OTHER INFORMATION: PCR primer

<400> SEQUENCE: 36
tcagtcgcca tcggatgttt                                                 20

<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37
accaatcttt cttcaacacg                                                 20
```

PROCESSES AND VECTORS FOR PLASTID TRANSFORMATION OF HIGHER PLANTS

CROSS-REFERENCE TO RELATED APPLICATIONS

The present application is a 35 U.S.C. § 371 National Phase Application of International Application Ser. No. PCT/EP02/00481, filed Jan. 18, 2002 and published in English as PCT Publication No. WO 02/057466 on Jul. 25, 2002, which claims priority to German Patent Application Ser. No. 101 02 389.8, filed Jan. 19, 2001, the disclosures of each of which are incorporated herein by reference in their entireties.

FIELD OF THE INVENTION

The present invention generally pertains to plant molecular biology and more particularly pertains to novel methods for plastid transformation.

BACKGROUND OF THE INVENTION

According to generally accepted knowledge, two classes of cell organelles, i.e. plastids and mitochondria, are derived from initially independent prokaryotes that were taken up into a predecessor of present day eukaryotic cells by separate endosymbiotic events (Gray, 1991). As a consequence, these organelles contain their own DNA, DNA transcripts in the form of messenger RNA, ribosomes, and at least some of the necessary tRNAs that are required for decoding of genetic information (Marechal-Drouard et al., 1991).

While, shortly after endosymbiotic uptake, these organelles were genetically autonomous, since they contained all the elements necessary to drive prokaryotic life, this autonomy was reduced during evolution by transfer of genetic information to the cell's nucleus. Nevertheless, their genetic information is of sufficient complexity to make recent cell organelles an attractive target for gene technology. This is particularly the case with plastids, because these organelles still encode about 50% of the proteins required for their main function inside the plant cell, photosynthesis. Plastids also encode their ribosomal RNAs, the majority of their tRNAs and ribosomal proteins. In total, the number of genes in the plastome is in the range of 120 (Palmer, 1991). The vast majority of proteins that are found in plastids are, however, imported from the nuclear/cytosolic genetic compartment.

Plastids can be Genetically Transformed

With the development of general molecular cloning technologies, it became soon possible to genetically modify higher plants by transformation. The main emphasis in plant transformation was and still is on nuclear transformation, since the majority of genes, ca. 26,000 in the case of *Arabidopsis thaliana*, the complete sequence of which was recently published (The Arabidopsis Genome Initiative, 2000), is found in the cell's nucleus. Nuclear transformation was easier to achieve, since biological vectors such as *Agrobacterium tumefaciens* were available, which could be modified to efficiently enable nuclear transformation (Galvin, 1998). In addition, the nucleus is more directly accessible to foreign nucleic acids, while the organelles are surrounded by two envelope membranes that are, generally speaking, not permeable to macromolecules such as DNA.

A capability of transforming plastids is highly desirable since it could make use of the enormous gene dosage in these organelles—more than 10000 copies of the plastome may be present per cell—that bears the potential of extremely high expression levels of trangenes. In addition, plastid transformation is attractive because plastid-encoded traits are not pollen transmissible; hence, potential risks of inadvertent transgene escape to wild relatives of transgenic plants are largely reduced. Other potential advantages of plastid transformation include the feasibility of simultaneous expression of multiple genes as a polycistronic unit and the elimination of positional effects and gene silencing that may result following nuclear transformation.

Methods that allow stable transformation of plastids could indeed be developed for higher plants. To date, two different Methods are available, i.e. particle bombardment of tissues, in particular leaf tissues (Svab et al., 1990), and treatment of protoplasts with polyethylene glycol (PEG) in the presence of suitable transformation vectors (Koop et al., 1996). Both methods mediate the transfer of plasmid DNA across the two envelope membranes into the organelle's stroma.

One significant disadvantage of all multicellular plant transformation procedures used today is the occurrence of marker genes in the transgenic plants. These marker genes that are needed for the selection of transgenic plant cells from a vast background of untransformed cells code for antibiotic or herbicide resistance genes. Examples for plastid resistance genes are aadA conferring resistance to spectinomycin and streptomycin (Svab & Maliga, 1993), or nptII conferring resistance to kanamycin (Carrer et al., 1993). As these marker genes are stably integrated into the genome together with the genes of interest (GOI), they will stay in the homoplastomic transgenic plants although they are not required for GOI function. These remaining marker genes are a main issue of criticism of plant biotechnology as they could theoretically increase antibiotic resistance of pathogens or herbicide resistance of weeds. Construction of a selection system which does not result in a resistance gene in the transgenic plant is, therefore, highly desirable (Iamtham and Day, 2000).

Another problem in plastid transformation is the shortage of selectable marker genes available. The aadA gene is the only selectable marker gene that is used routinely (Heifetz, 2000), and the nptII gene is the only alternative that has been shown to function in higher plant plastid transformation (Carrer et al., 1993). Since neither the aadA nor the nptII gene can be used universally, the number of higher plant species that have been transformed in the plastome is still very low (Heifetz, 2000). Plastid transformation in higher plants cannot at present be exploited to its full potential.

SUMMARY OF THE INVENTION

It is an object of this invention to provide a simple, yet highly versatile process for producing genetically stable multicellular plants, plant organs or plant tissues transformed in their plastome, which are free of a foreign gene required for selection such as an antibiotic or herbicide resistance gene.

This object is achieved by a process for producing multicellular plants, plant organs or plant tissues transformed in their plastome by the following steps:

(a) altering or disrupting the function of a gene in a plastid genome for producing a selectable or recognizable phenotype;

(b) separating or selecting plants or cells having plastids expressing said phenotype;

(c) transforming said plastid genome of said separated or selected plants, seeds, cells or plastids with at least one transformation vector having a restoring sequence capable of restoring said function; and (d) separating or selecting said transformed plants or cells having plastids expressing said restored function.

Preferred embodiments are defined in the subclaims.

It is surprising that this new method is readily applicable to multicellular plants, plant organs, or plant tissue since these contain a plurality of plastids in each cell, which means that segregation of genotypes is required on the level of plastomes, the level of plastids and the level of cells. It has been found that this new process is highly efficient for the tissue of higher plants since segregation occurs readily during growth. Separation is therefore simply possible by optical inspection and manual manipulation in appropriate embodiments. In cases of inhibitor-supported selection (step (b)), the selection process can be carried out rapidly since in the case of multicellular plants, plant organs or plant tissue the inhibitor does not need to be applied throughout the whole regeneration process, but may be applied only initially. (Of course, as explained above, it is possible to avoid inhibitors completely.) This shows a close combination effect between multicellularity and the method of transformation.

In the case of a transformation of a plant tissue by the process of the invention, the consequences of alteration or disruption of a gene, which may frequently be lethal in the case of a single isolated cell if this gene is of central importance e.g. for a metabolic pathway, are mitigated by the fact that a single transformed cell does not stand in isolation. Rather, it is part of a population of cells among which metabolites may be exchanged.

There are many different plastid genes which can be altered or disrupted for the purposes of this invention. Such a gene should be important for plastid function in the sense of producing a selectable or recognisable phenotype upon alteration or disruption. Such a function may be any function which is plastid encoded. Preferably, this function is directly or indirectly involved in photosynthesis. Examples for functions indirectly necessary for photosynthesis are any functions needed for transcription and/or translation of plastid genes. Examples for functions directly involved in photosynthesis are any proteins which are essential, at least under selection conditions, for photosynthesis.

Preferably, said recognisable phenotype is easily discernable. Since said function above is preferably directly or indirectly associated with photosynthesis, an easily recognisable phenotype may be pigment deficiency, most preferably chlorophyll deficiency or altered fluorescence. The transformed plant may then be grown heterotrophically and transformed plants, plant organs or plant tissue may be separated or selected for. Separation may be effected manually by optical recognition of transformed tissue areas. Selection may be effected via inhibitor resistance based on a resistance gene introduced in step (a) of the process of this invention. Alternatively, inhibitor resistance may be a consequence of said altered or disrupted function itself.

After reaching the homoplastomic state by segregation during several rounds of regeneration, the transgenic plant, plant organ or plant tissue is transformed a second time (step (c)), whereby the altered or disrupted function is restored and the marker gene, if any, is removed. The transformed plants, plant organs or plant tissues having the restored phenotype, e.g. phototrophy, are subsequently separated or selected.

Additional sequences or genes of interest may be introduced in step (a) and/or step (c) e.g. for expressing a desired gene, for conferring a useful trait or for any other desired plastome modification.

Further, sequences introduced in step (a) and step (c) may together result in an additional function. Examples for this embodiment include the following: introducing sequences in step (a) and step (c) that code for different subunits of a multi-subunit protein; providing regulatory sequences in step (a) or step (c) that make a coding sequence introduced in step (c) or step (a), respectively, expressible; introducing sequences in steps (a) and (c) that code for proteins of a biochemical pathway; etc.

Specific examples of the function to be disrupted may be knock outs of rpoA or rpoB. These genes code for the $\alpha$ and $\beta$ subunit, respectively, of the plastid encoded plastid RNA polymerase. Plastids lacking these genes are not able to conduct photosynthesis, show an albino phenotype, and are not able to grow phototrophically. After restoration of rpoA or rpoB in the second round of transformation, the transgenic plants are able to grow phototrophically in light and show a green phenotype.

Another example of a target gene for step (a) may be a knock out of ycf3. This gene is not essential under normal light conditions (Ruf et al., 1997). Nevertheless, if a ycf3 knock out mutant is placed under strong light, it develops an albino phenotype and growth is repressed under photosynthetic growth conditions. Plants with restored ycf3 gene are able to grow phototrophically under strong light conditions. So in this case, the selection pressure for the second transformation can be adjusted by the light intensity. Therefore, in contrast to the example using rpoA or rpoB, the second transformation can be carried out with green, normally growing plant mutants when kept under low light conditions and selection pressure can be raised after a regeneration time simply by increasing the light intensity. As the condition of the plant material is critical for transformation, this method is superior to transformation of albino material.

Another example for the function to be altered or disrupted is a knock out of petA in the first round of transformation (step (a)). petA encodes a subunit of the cytochrome b/f complex. petA knock out mutants show a high chlorophyll fluorescence phenotype (hcf) and are not able to conduct photosynthesis. Therefore, they are not able to grow phototrophically. The phototrophic growth in light is restored, when petA is restored in the second round of transformation (step (c)).

Definitions

The following definitions are given in order to clarify the meanings of certain terms used in the description of the present invention.

| | |
|---|---|
| 3'-UTR | transcribed but not translated region of a (→) gene, downstream of a (→) coding region; in (→) plastid (→) genes, the 3'-UTR a.o. serves to stabilise the mRNA against 3' to 5' exonucleolytic degradation |

-continued

| | |
|---|---|
| 5'-UTR | transcribed but not translated region of a (→) gene, upstream of a (→) coding region; in (→) plastid (→) genes, the 5'-UTR contains sequence information for translation initiation (ribosome binding site, (→) RBS) close to its 3' end |
| aadA | (→) coding region of bacterial aminoglycoside adenyl transferase, a frequently used protein, that detoxifies antibiotic (→) selection inhibitors spectinomycin and/or streptomycin |
| chloroplast | (→) plastid containing chlorophyll |
| coding region | nucleotide sequence containing the information for a) the amino acid sequence of a polypeptide or b) the nucleotides of a functional RNA; coding regions are optionally interrupted by one or more (→) intron(s) |
| desired gene, (sequence) | modified or newly introduced sequence: the purpose of a (→) transformation attempt |
| flank, flanking region | DNA sequences at the 5' and 3' ends of inserts in a (→) plastid (→) transformation (→) vector, which mediate integration into the target (→) plastome of sequences between the flanks by double reciprocal (→) homologous recombination. By the same mechanism, sequences can be modified or removed from the target (→) plastome. Thus, the flanks of the (→) plastid (→) transformation (→) vector determine, where changes in the target (→) plastome are generated by (→) transformation. |
| gen xpr ssion | process, turning sequence information into function; in (→) genes encoding polypeptides, gene expression requires the activity of a (→) promoter which initiates and directs RNA polymerase activity, leading to the formation of a messenger RNA, which is subsequently translated into a polypeptide; in (→) genes encoding RNA, the (→) promoter-mediated activity of RNA polymerase generates the encoded RNA |
| gene(s) | nucleotide sequence(s) encoding all elements, which are required to secure function independently; genes are organised in (→) operons, which contain at least one complete (→) coding region in (→) genes encoding polypeptides, these elements are: (1) a (→) promoter, (2) a 5' untranslated region ((→) 5'-UTR), (3) a complete (→) coding region, (4) a 3' untranslated region ((→) 3'-UTR); in (→) genes encoding RNA, the (→) 5'-UTR and the (→) 3'-UTR are missing; in (→) operons consisting of more than one (→) coding region, two subsequent complete (→) coding regions are separated by a (→) spacer, and (→) promoter, (→) 5'-UTR, and (→) 3'-UTR elements are shared by the (→) coding regions of that (→) operon. |
| genome | Complete DNA sequence of a cell's nucleus or a cell organelle |
| hcf | high chlorophyll fluorescence; hcf mutants show a characteristic photosynthesis deficient phenotype |
| heteroplastomic plastid/cell | a (→) plastid or cell containing genetically different plastomes |
| homologous recombination | process leading to exchange, insertion or deletion of sequences due to the presence of (→) flanks with sufficient sequence homology to a target site in a (→) genome |
| homoplastomic plastid/c ll | a (→) plastid or cell containing genetically different plastomes |
| ins rtion sit | locus in the (→) plastome, into which novel sequences are introduced |
| interg nic region | sequences between two (→) g nes in a (→) g nome; such region occur as (→) int r peronic regions or as (→) intraoperonic regions, in which case they are also called (→) spacers |
| intragenic region | sequences inside a (→) gene |
| intron | sequence interrupting a (→) coding region |
| organ | a plant organ is a structure that serves a special biological function and consists of one or more characteristic (→) tissues; examples are: root, stem, leaf, flower, stamen, ovary, fruit etc. |
| operon | organisational structure of (→) genes |
| petA | (→) coding region of the (→) plastid (→) gene for the cytochrome f protein involved in photosynthetic electron transport |
| plant(s) | organism(s) that contain(s) (→) plastids in its cells; this invention relates to multicellular (→) plants; these include the group of gymnosperms (such as pine, spruce and fir etc.) and angiosperms (such as *monocotyledonous* crops e.g. maize, wheat, barley, rice, rye, Triticale, sorghum, sugar cane, asparagus, garlic, palm tress etc., and non-crop monocots, and *dicotyledonous* crops e.g. tobacco, potato, tomato, rape seed, sugar beet, squash, cucumber, melon, pepper, Citrus species, egg plant, grapes, sunflower, soybean, alfalfa, cotton etc.), and non-crop dicots as well as ferns, liverworts, mosses, and multicellular green, red and brown algae. |
| plastid(s) | organelle(s) with their own genetic machinery in (→) plant cells, occurring in various functionally and morphologically different forms, e.g. amyloplasts, (→) chloroplasts, chromoplasts, etioplasts, gerontoplasts leukoplasts, proplastids etc. |

-continued

| | |
|---|---|
| plastome | complete DNA sequence of the (→) plastid |
| promoter | nucleotide sequence functional in initiating and regulating transcription |
| RBS, ribosomal binding site | DNA sequence element upstream of the (→) translation start codon of a (→) coding region, that mediates ribosome binding and translation initiation from the respective RNA transcript; RBS elements are either part of (→) 5'-UTRs or of spacers. |
| rpoA/B/C | (→) coding regions of the (→) plastid (→) genes for the plastid encoded RNA-Polymerase (PEP) |
| selection inhibitor | chemical compound, that reduces growth and/or development of non-transformed cells or organelles stronger than that of transformed ones |
| tissue | a plant tissue consists of a number of cells with similar or identical structure and function; cells in plant tissues are connected by plasmodesmata; examples are: callus, palisade parenchyma, spongy parenchyma, cambium, epidermis, pith, endosperm, phloem, xylem etc. |
| transformation vector | cloned DNA molecule that was generated to mediate (→) transformation of a (→) genome; |
| transformation | process leading to the introduction, the excision or the modification of DNA sequences by treatment of (→) plants or plant cells including the use of at least one (→) transformation vector |
| transgene | DNA sequence derived from one (→) genome, introduced into another one |
| translation start codon | sequence element, that encodes the first amino acid of a polypeptide |
| translation stop codon | sequence element that causes discontinuation of translation |
| uidA | (→) coding region of bacterial β glucuronidase, a frequently used reporter protein |
| ycf3 | (→) coding region for a protein that is involved in PSI assembly; Δycf3 lines display a pale phenotyp and growth depression, when cultivated under standard light conditions (3.5–4 W/m$^2$). Under low light conditions (0.4–0.5 W/m$^2$) the phenotype is much less severe. |

SHORT DESCRIPTION OF THE FIGURES

Figure 2:
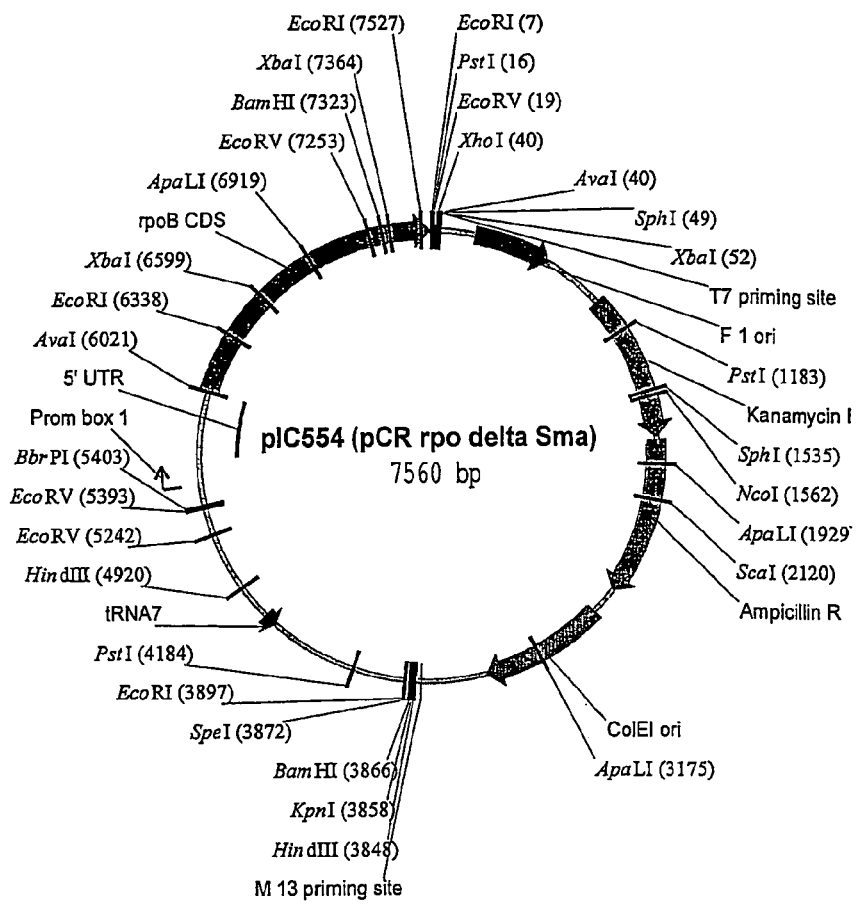
Figure 3:
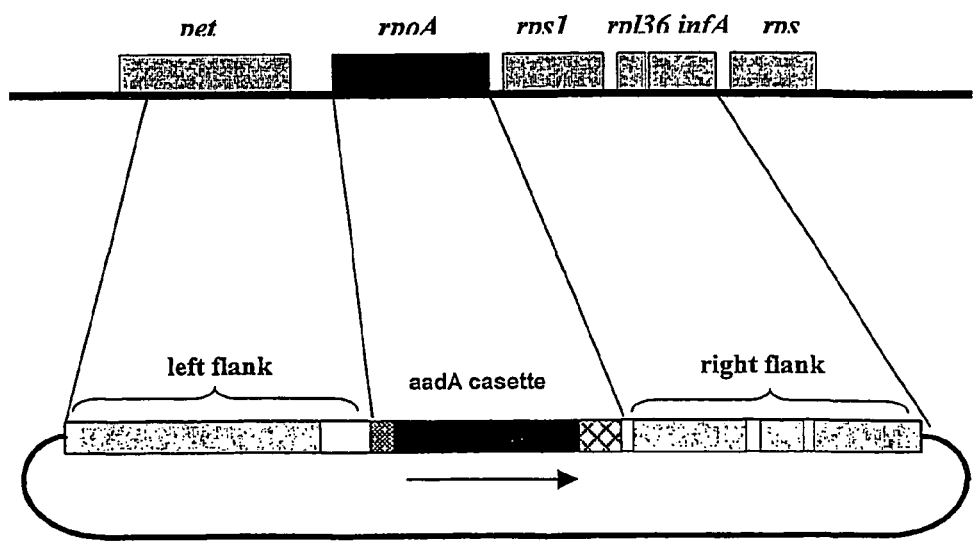
Figure 4:
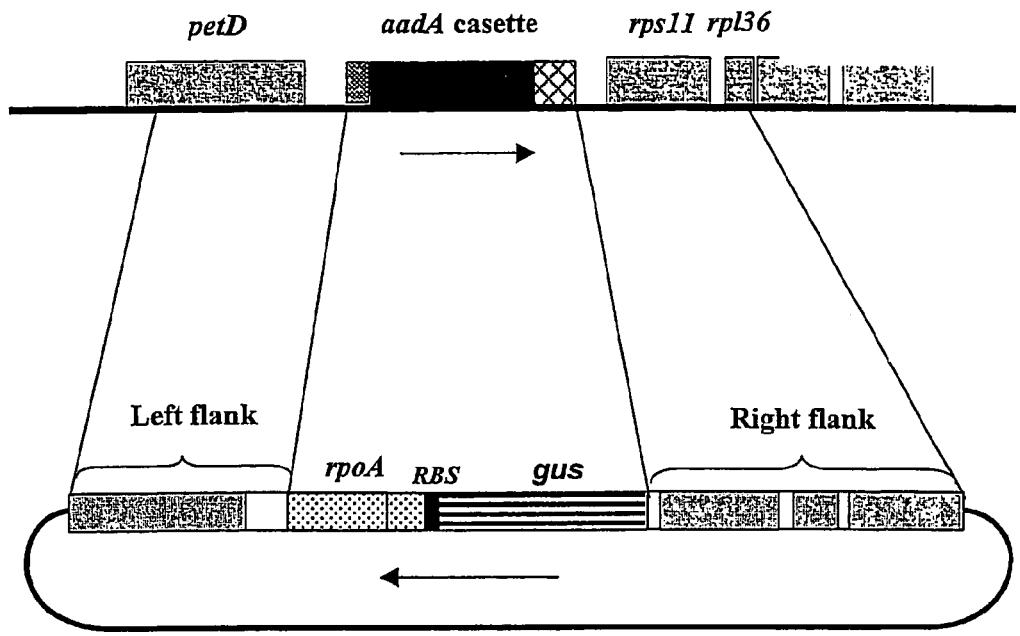
Figure 5:
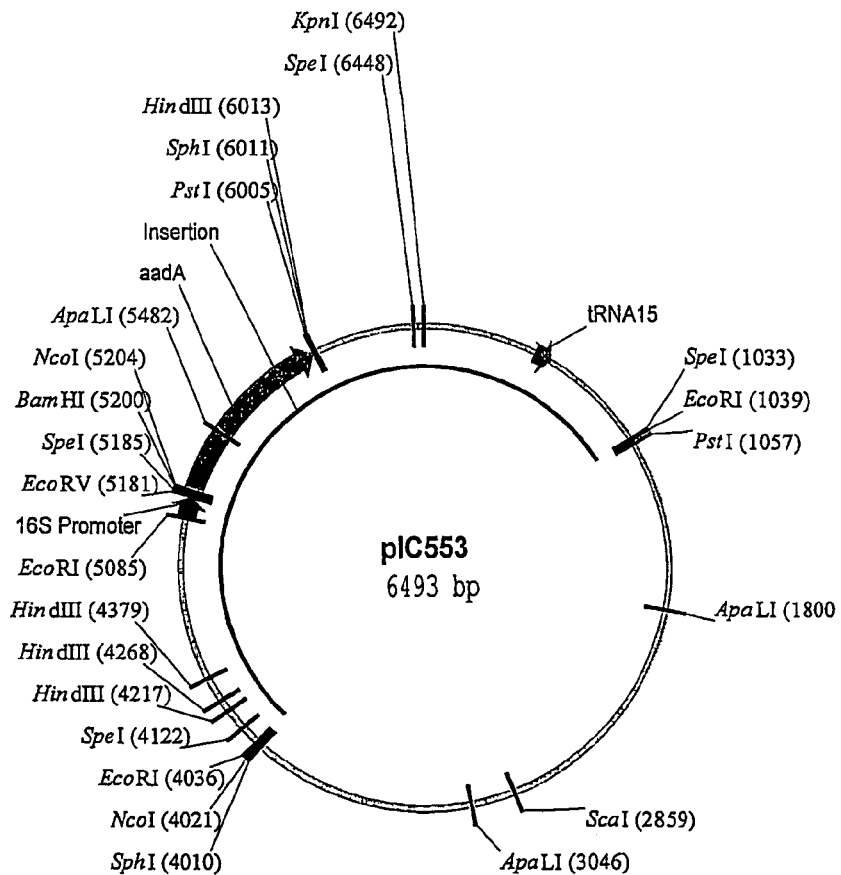
Figure 6:
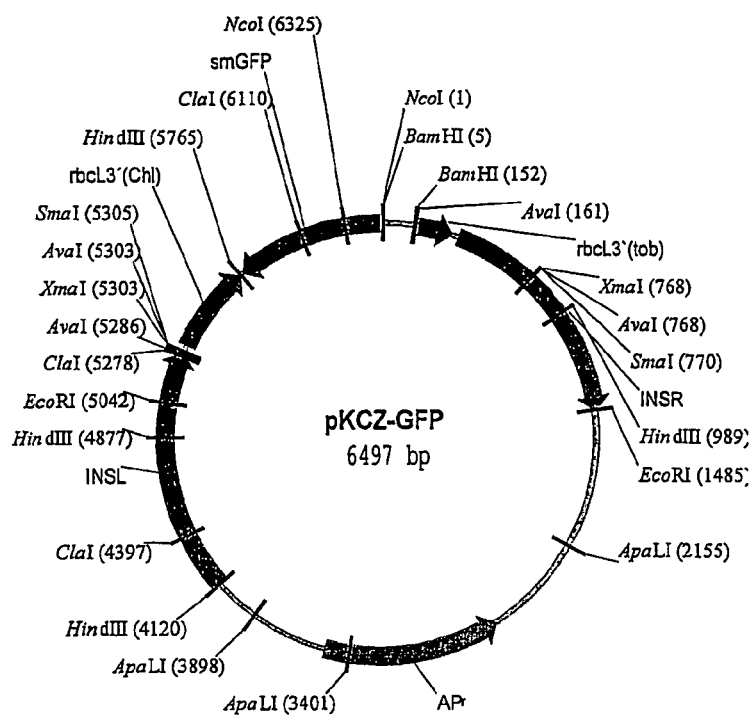
Figure 7:
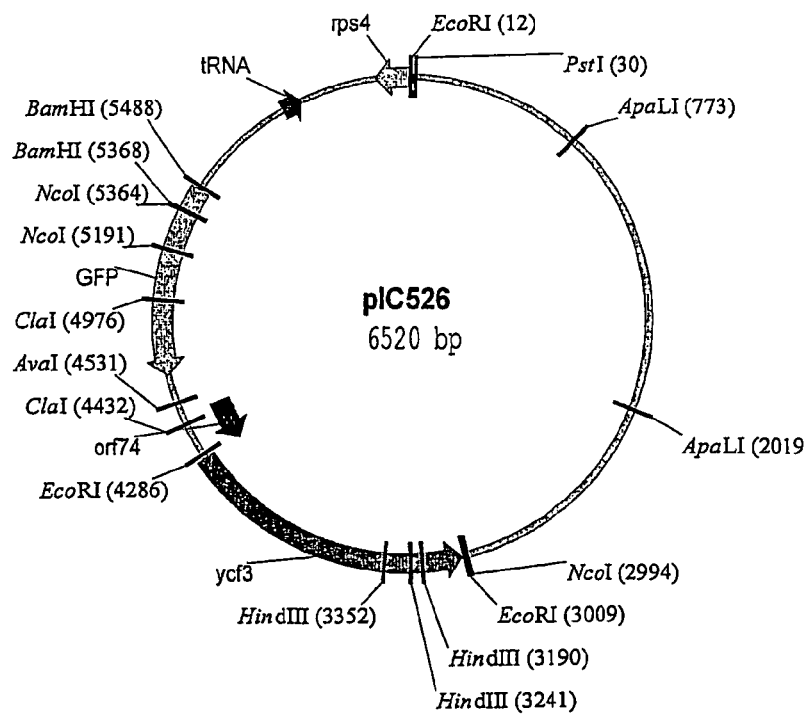
Figure 8:
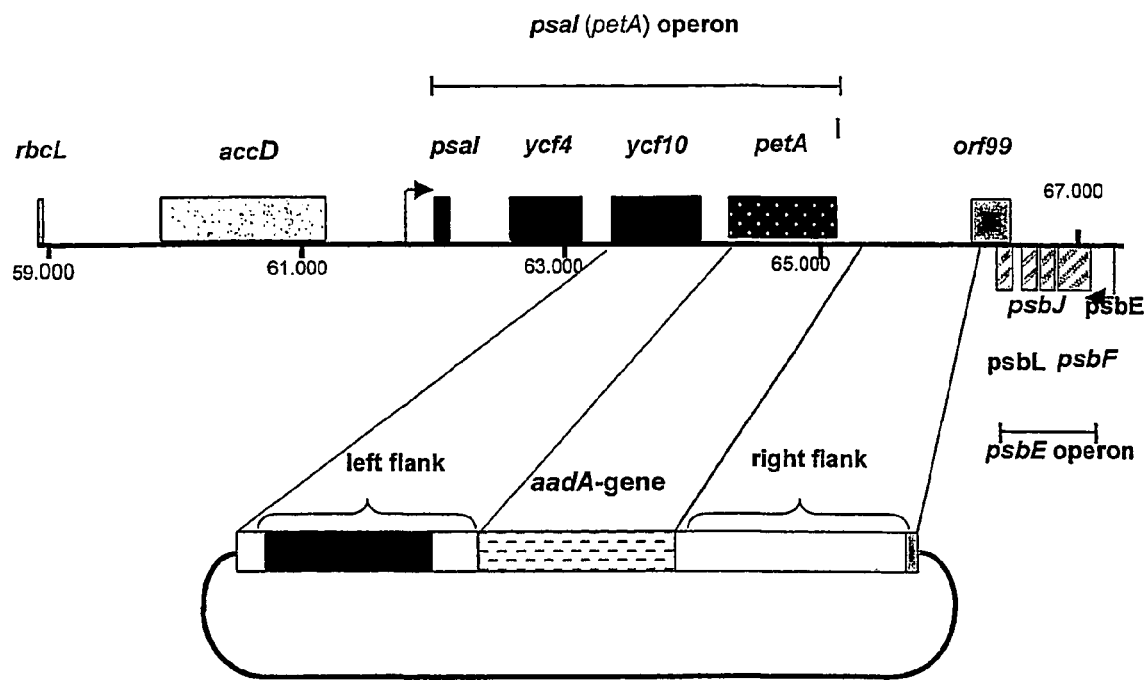
Figure 9:
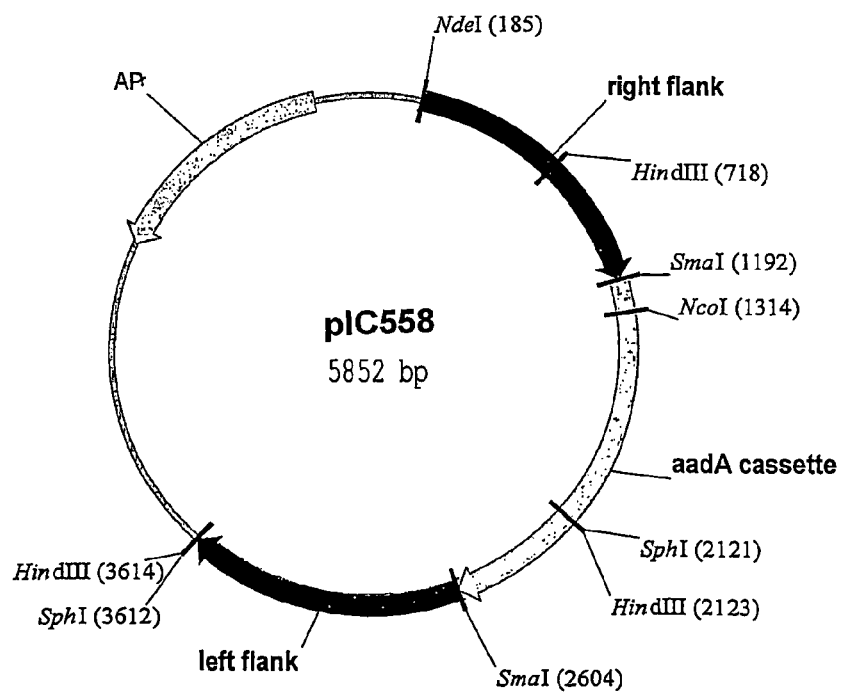
Figure 10:
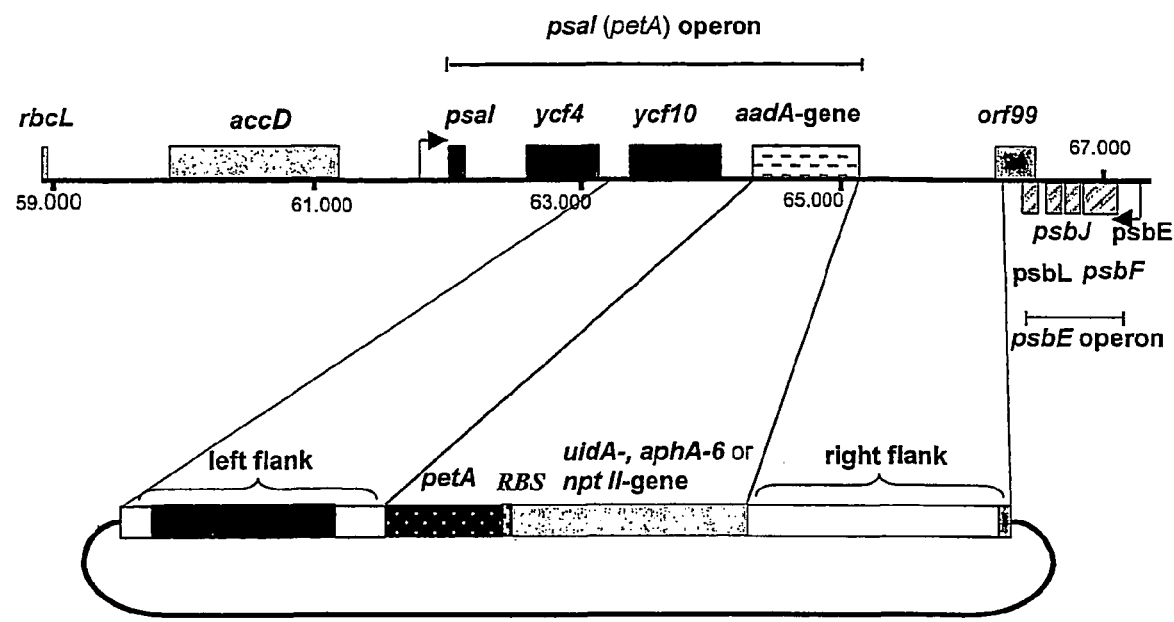
Figure 11:
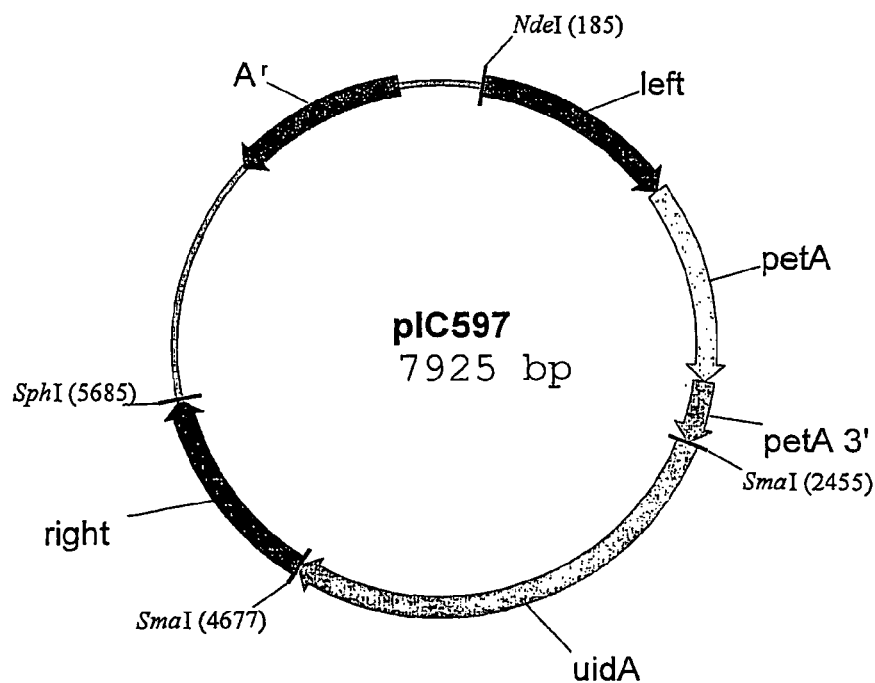
Figure 12:
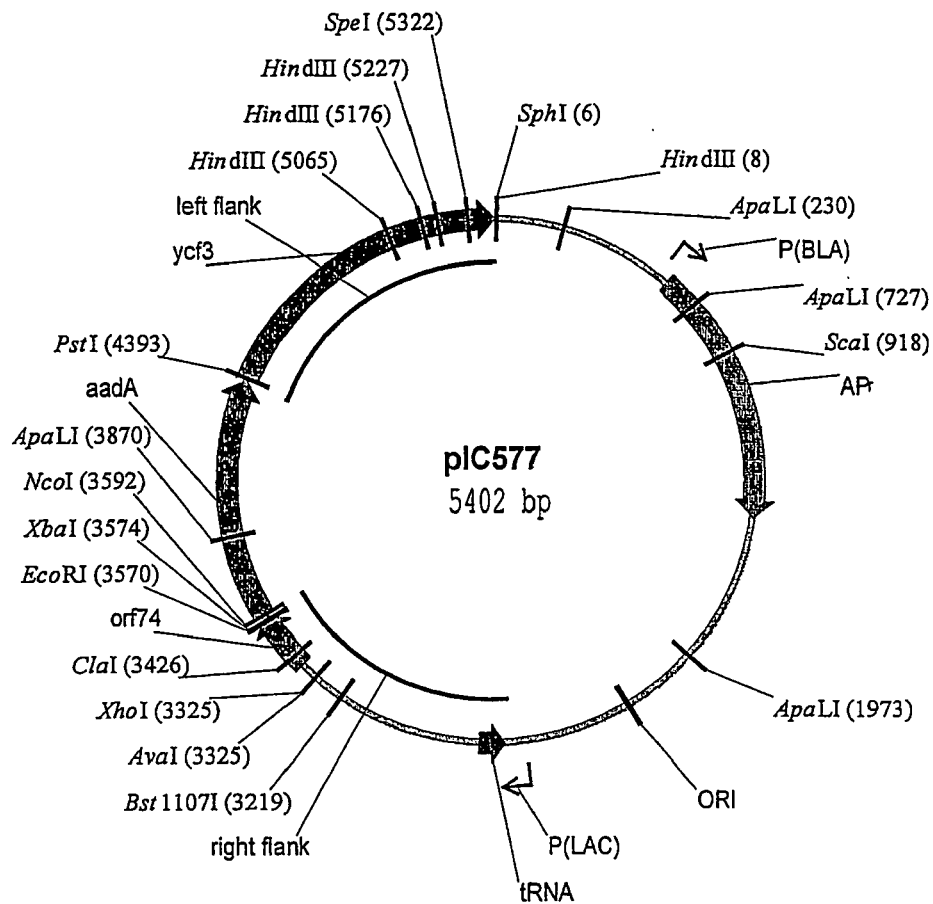
Figure 13:
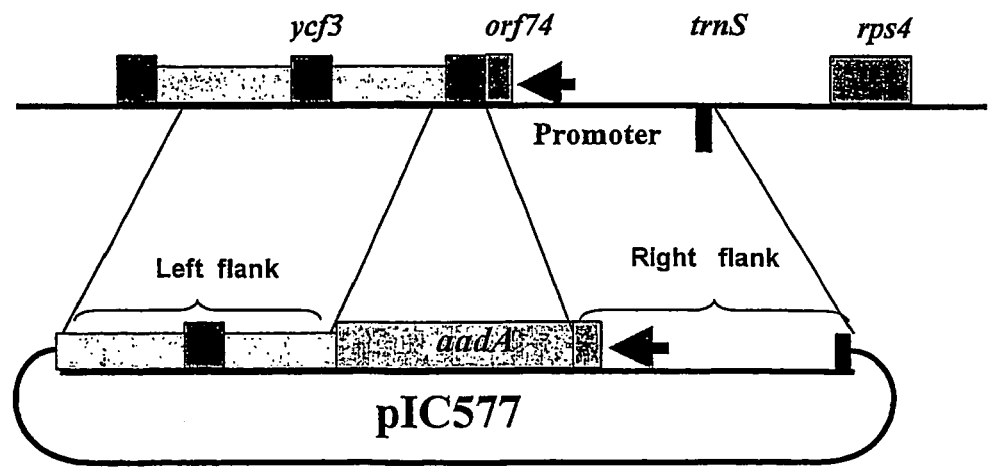
Figure 14:
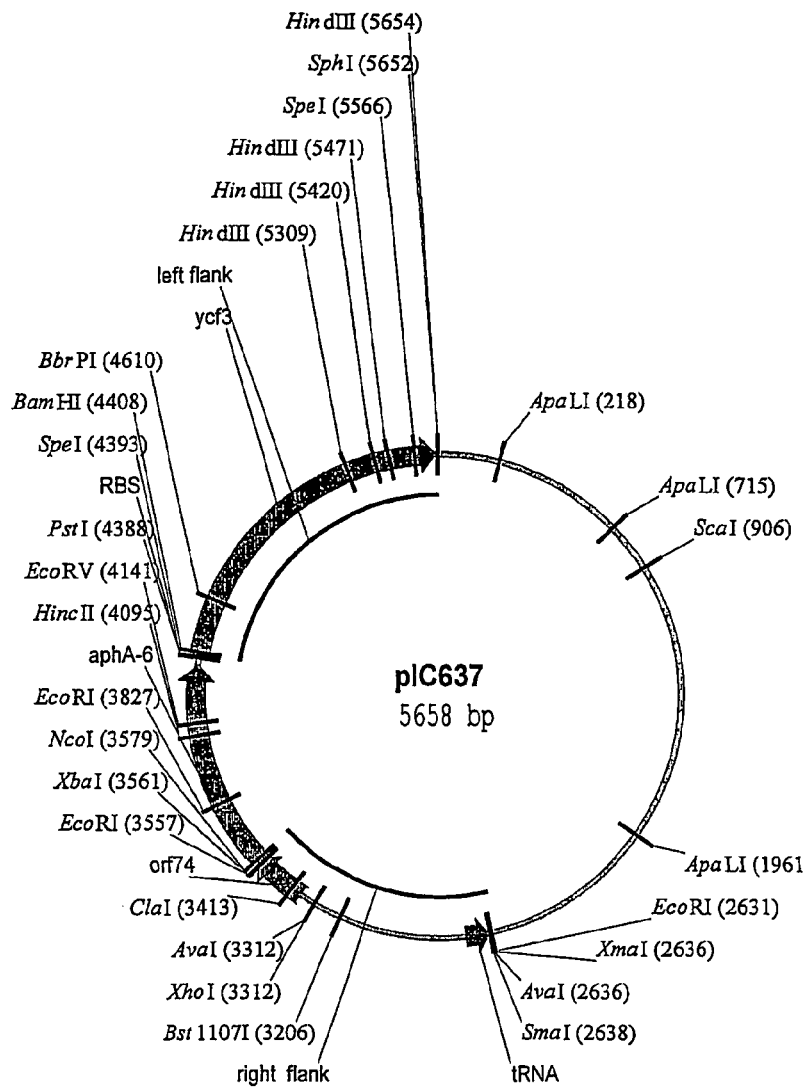
Figure 15:
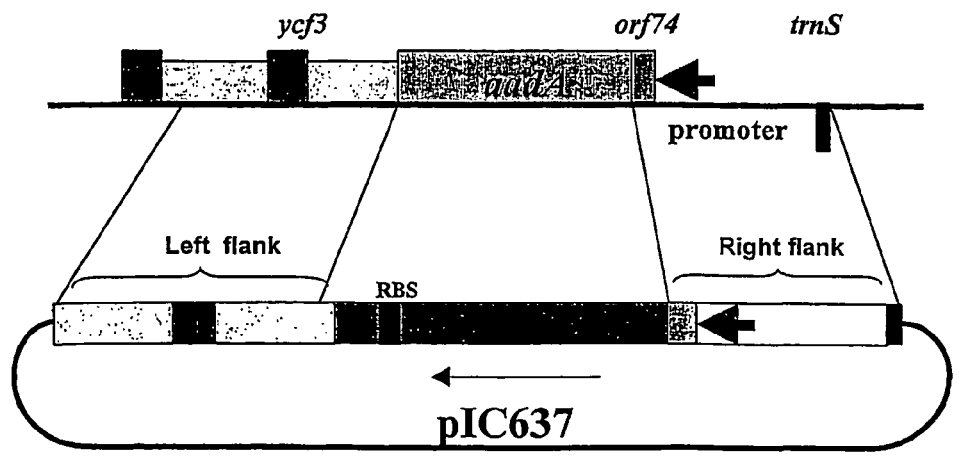

FIG. 1: Schematic view of vector pIC571.
FIG. 2: Schematic view of vector pIC554.
FIG. 3: Schematic view of vector pGEM-rpoA-del and targeted plastome region.
FIG. 4: Schematic view of vector pIC598 and targeted plastome region.
FIG. 5: Schematic view of vector pIC553.
FIG. 6: Schematic view of vector pKCZ-GFP.
FIG. 7: Schematic view of vector pIC526.
FIG. 8: Schematic view of vector pIC558 and targeted plastome region.
FIG. 9: Schematic view of vector pIC558.
FIG. 10: Schematic view of vectors pIC597, pIC599 and pIC600 and targeted plastome region.
FIG. 11: Schematic view of vector pIC597.
FIG. 12: Map vector pIC577.
FIG. 13: Schematic view of vector pIC577 and targeted plastome region.
FIG. 14: Map of vector pIC637.
FIG. 15: Schematic view of vector pIC637 and targeted plastome region.

DETAILED DESCRIPTION OF THE INVENTION

Vectors of this Invention Provide a Visible Marker During Selection

Non-lethal inhibitor concentrations that do not kill plant cells but inhibit growth to a certain degree can be used for plastid transformation. Only one or a few of the up to 10,000 plastome copies per cell can be assumed to be recombinant after the initial transformation event. Treating the cultured cells or tissues with a lethal inhibitor concentration after transformation would not allow to recover heteroplastomic cells expressing a moderate resistance, which is due to a low number of transformed plastome copies. Selection and segregation leads to the occurrence of both wild-type and transplastomic tissues. It is a major problem to discriminate between wild-type and transgenic tissue during this process, because transformed plastids may mask wild type ones. Khan and Maliga (1999) used a fluorescent antibiotic resistance marker, comprising the aadA and GFP coding regions, to track segregation in plastid transformants under UV-light. In this invention, we present a visible marker for the transplastomic tissue sectors which can be detected by the naked eye. The gradual process of sorting out wild-type and recombinant plastids can easily be monitored and thus be accelerated. The appearance of green sectors on the white background of the mutant phenotype can be easily detected.

Vectors of this Invention Provide Improved Regeneration Efficiency

Conventional chloroplast transformation strategies are based on the selection for resistance against an inhibitor, e.g. spectinomycin. Inhibitor application starts after transformation and is perpetuated during the whole process of repetitive regenerations which are necessary to obtain a homoplastomic genotype. Inhibitor application has the disadvantage to reduce the regeneration potential. Regeneration of whole plants from single protoplasts or leaf pieces is a critical step in chloroplast transformation, particularly when extending the method to species, for which established and reliable regeneration protocols do not exist. It is a major advantage of this invention, that inhibitors may only have to be utilized during a short period after the first transformation. Using our novel methods, inhibitor application can be omitted during repetitive regeneration in order to achieve a homoplastomic condition and during the complete second transformation step.

Vectors of this Invention Allow Generation of Genetically Stable Plastome Transformants Homologous recombination in plastids is known to occur with high efficiency. As a consequence, undesired recombination events between regulatory elements of an antibiotic resistance marker and endogenous regulatory elements may lead to genetic instability (Eibl et al., 1999). After the second transformation step the transplastomic plant does not contain any marker expression cassette. Consequently the final transformants contain fewer regions of homology than conventional plastid transformants. The genetic stability of the transformants is increased and undesired loss of sequences (Eibl et al., 1999) is avoided.

By this invention, a novel antibiotic-free, photosynthesis related selection system for chloroplast transformation of higher plants can be provided. The new system utilizes visible markers and may be based on the inactivation of genes like rpoA, rpoB, ycf3 or petA yielding a white or pale phenotype. In a second step, the respective deficient gene of the mutant line may be restored and one or more transgenes may be inserted. The resulting transplastomic plants may be free of an antibiotic resistance gene.

Other possible target functions for step (a) of the process of this invention are any plastid encoded functions which are directly or indirectly required for photosynthesis. Apart from the specific applications described below, inactivation and restoration of numerous photosynthesis related target genes, such as e.g. psbA may be used according to this invention.

Plastid chromosomes encode four RNA polymerase genes, designated rpoA, B, C1 and C2, that resemble the three RNA polymerase core genes of eubacteria. The genes for rpoB, C1 and C2 are arranged in an operon (transcribed by NEP, a nuclear encoded plastid RNA polymerase), while the gene for rpoA is located in a large cluster of genes that mainly encode ribosomal proteins. Since the level of the sense transcript of the rpoA gene decreases in PEP (plastid encoded plastid RNA polymerase) deficient mutants (Krause et al., 2000), rpoA might be transcribed by PEP.

Deletion of rpoA, rpoB or rpoC1 from the plastid genome results in a pigment-deficient phenotype (Allison et al., 1996; De Santis-Maciossek et al., 1999). The pigment-deficient ΔrpoA, ΔrpoB or ΔrpoC1 plants (white plants) are unable to grow photoautotrophically. However, if maintained on sucrose-containing medium to compensate for the lack of photosynthesis, they grow normally but at a reduced rate compared with wild-type plants.

ycf3 has recently been shown to be required for stable accumulation of the photosystem I (PSI) complex in tobacco (Ruf et al., 1997). Disruption of this gene leads to a conditional pigment-deficient phenotype in light. Homoplasmic ycf3 plants display a completely white phenotype upon regeneration on drug- and phytohormone-free medium under standard light conditions (3.5–4 W/m$^2$), while the phenotype is much less severe (light green) under low light conditions (0.4–0.5 W/m$^2$).

A mutant plant phenotype which is called hcf (high chlorophyll fluorescence) is well known. This phenotype is due to a mutation in expression and/or processing of photosynthesis related genes (either nuclear or plastome encoded genes; Bock et al. 1994; Monde et al., 2000; Monde et al., 2000b). These mutants show a characteristic photosynthesis deficient phenotype: impaired growth under greenhouse conditions, pale green leaves, and high chlorophyll fluorescence (red fluorescence) under UV-light illumination. Hcf appears when the photosynthetic electron transport chain is blocked ('electron tailback'). One possibility to achieve a hcf phenotype is to inactivate the plastid petA gene, which codes for a subunit of the cytochrome b/f complex involved in photosynthetic electron transport.

Taking advantage of the pigment or photosynthesis deficient phenotypes of, for example, Δrpo, Δycf3 or ΔpetA plants, a second round of transformation may be performed using the first round pigment-deficient transformants as a substrate to restore the deficiency, remove the selection marker of the first round, if any, and optionally introduce sequences of interest simultaneously. Green plants can be recovered by delivering a wild type gene into the plastome of pigment-deficient mutants. Therefore, such secondary transformants will regain the ability of photosynthetic growth and display a green phenotype and/or normal chlorophyll fluorescence in case of the hcf phenotype. This characteristic can be used to select transformed tissues. Thus no antibiotic selection is required in this second step. More importantly, selection markers used during the first round of transformation can be removed in the second round, yielding marker-free transplastomic plants.

Plastid gene transformation is based on homologous recombination. This can be achieved by using, in a transformation vector, flanking regions of sufficient homology to target sites on the plastome, which is well-known in the art. In the present invention, transformation may be performed by any method known in the art. Presently, there are two such known methods, namely particle gun transformation and PEG-mediated transformation. In this invention, particle gun transformation is preferred. Both steps (a) and (c) of the process of this invention may also be achieved by co-transformation, i.e. using more than one transformation vector.

The teaching of this invention may be applied to any multicellular plant. Preferred plants are monocot and dicot crop plants. Specific examples of crop plants are listed herein under item "plants" in section "Definitions".

There are several possibilities for altering or disrupting the function of a plastid gene in step (a) provided that a selectable or recognizable phenotype is produced. Examples include partial or full deletion of the coding region of said gene or of a functional element required for expression of said gene e.g. promoter, 5'-UTR, 3'-UTR, and start codon. The function of these elements may also be altered or disrupted by insertion of a foreign sequence into these elements or the coding region, by full or partial replacement of these elements by a foreign sequence or by insertion of a stop codon into the coding region. The above means may also be combined. If a resistance marker gene is introduced in step (a), the marker gene is preferably used as said foreign sequence. In step (a) any additional sequence of interest may be inserted concomitantly.

Step (a) of the process of this invention is preferably achieved by genetic transformation. In an alternative embodiment, step (a) may occur or may have occurred by a spontaneous or induced mutation. This means that a plant (or plant organs or plant tissue) used for step (c) of this invention may be a natural mutant or a transgenic plant not obtained according to this invention or for purposes of this invention, which is predominantly the production of transgenic plants free of a marker gene.

In step (b) of the process of this invention, plants, plant organs or plant tissue having plastids expressing the phenotype of interest are separated or selected for on medium supporting heterotrophic growth. Selection may be done using a selectable marker gene introduced in step (a) and a suitable antibiotic or inhibitor. Alternatively, the novel procedures of this invention using photosystem I acceptor herbicides as described in more detail below may be applied. In the latter case, no resistance gene has to be introduced in step (a). As described above, inhibitors or antibiotics do only have to be utilized during a short period after the first transformation to support segregation and the use of such an agent can even be neglected totally. After growth and several cell divisions, segregation leads to the formation of zones differing in pigment abundance or fluorescence. Tissue from such zones is separated manually and is used for further rounds of regeneration.

In step (c) of the process of this invention, the plastome of a plant obtained in previous steps is transformed with a vector having a restoring sequence capable of restoring the function altered or disrupted in step (a). Said restoring may be achieved by several means dependent on how alteration or disruption in step (a) was done. Inserted sequences may be removed, replaced sequences may be replaced again with the original fully functional sequence, and deleted sequences may be reinserted. Concomitantly, a resistance gene inserted in step (a) may be removed or its function may be destroyed and an additional genetic modification of the plastome may be carried out or an additional function may be introduced. Examples include introduction of an additional sequence or gene of interest, introduction of several genes, elimination of a preexisting function or sequence etc.

In step (d), plants, plant organs or plant tissue having plastids expressing said restored function are separated or selected for on antibiotic-free medium. Selection may be achieved by at least partial phototrophic growth and transformed plants are recognizable by the restored phenotype. Upon growth, segregation leads to the formation of zones of differing pigment abundance. Green zones are separated manually and used for further rounds of regeneration. In this invention, the conditions used in step (d) are preferably mixotrophic. This means that the carbohydrate content of the medium is lowered as much as possible such that plastids containing transformed plastomes and cells containing transformed plastids which have regained the ability for photosynthesis have a selective growth advantage under strong light. Such mixotrophic conditons may accelerate step (d).

Embodiment 1: Method for the Selection of Plastid Transformants Based on the Inactivation and Restoration of the rpoA or rpoB Genes For targeted disruption of rpoB gene function, the rpoB promoter and the start codon may for example be replaced with the aadA marker gene or another marker gene. Bombarded leaf tissue may be regenerated under temporary selection on spectinomycin-containing medium in case of the aadA marker. Transformants display antibiotic resistance and initially a green phenotype in light while still being heteroplastomic. These primary transformants contain a mixture of both wild-type and transformed chloroplast genomes. The green, heteroplastomic material is transferred to non-selective medium. Segregation leads to the occurrence of white, mixed, and green sectors. Material from white sectors may be subjected to several additional rounds of regeneration on non-selective medium in order to obtain homoplastomic mutant transformants.

In the second transformation, the homoplastomic ΔrpoB plants may be transformed with a vector designed to reconstitute the rpoB gene, remove the marker gene and preferably introduce a gene (or genes) of interest at the same time. The treated leaf tissue may be regenerated under selection on sucrose-reduced medium (antibiotic free) under strong light. Transformants which display a green phenotype and are able to grow photoautotrophically may be selected.

A disruption and reactivation of the rpoA gene may be achieved in a similar way.

Embodiment 2: Method for the Selection of Plastid Transformants Based on the Inactivation and Restoration of the ycf3 Gene Disruption of ycf3 gene may be achieved by replacing the 5'-regulatory element and the first exon of ycf3 by a marker gene like the aadA marker gene. The transformation vector may be introduced into tobacco plastids e.g. using the biolistic protocol or PEG-mediated transformation. The bombarded leaf tissue, in case of the biolistic protocol, is regenerated under selection on medium containing an inhibitor or antibiotic, spectinomycin in case of the aadA gene. Transformants display inhibitor resistance and initially a green phenotype under standard light conditions (3.5–4 W/m$^2$) while still being heteroplastomic. These primary transformants normally contain a mixture of wild-type and transformed chloroplast genomes. After transfer to antibiotic-free medium, segregation leads to the occurrence of yellow-white and green sectors (under standard light conditions; see above). Material from white sectors may be subjected to several additional rounds of regeneration on non-selective medium in order to obtain homoplastomic mutant transformants. Besides having a pale, nearly white phenotype in light, the mutants show depressed growth. To obtain adequate material for the second transformation step, the mutant plant line may be transferred to low light conditions. Under these conditions (0.4–0.5 W/m$^2$), the plants show a much less severe phenotype and can yield suitable donor material e.g. for particle gun transformation. In this second transformation, the homoplastomic Δycf3 plants are transformed with a vector designed to reconstitute the ycf3 gene, remove the marker gene and preferably introduce a gene (or genes) of interest at the same time. The bombarded leaf tissue may be regenerated under selection on sucrose-reduced medium (antibiotic free) under strong light. Transformants, which display a normal green phenotype and are able to grow photoautotrophically, may be selected.

Embodiment 3: Method for the Selection of Plastid Transformants Based on the Inactivation and Restoration of the petA Gene For targeted disruption of the petA gene, the coding region may be replaced with a marker gene, e.g. the aadA marker gene. Bombarded leaf tissue, in the case of transformation by particle bombardment, may be regenerated under selection on antibiotic containing medium. Transformants display antibiotic resistance and initially a normal green phenotype in light while still being heteroplastomic. These primary transformants contain a mixture of wild-type and transformed chloroplast genomes. After transfer to antibiotic-free medium, segregation may lead to the occurrence of sectors displaying the hcf phenotype, which can be detected under UV illumination. Material from the mutant sectors may be subjected to several additional rounds of regeneration on non-selective medium in order to obtain homoplastomic mutant material.

In the second transformation, the homoplastomic ΔpetA plants may be transformed by bombardment with a transformation vector designed to reconstitute the ΔpetA gene, remove the marker gene and preferably introduce a gene (or genes) of interest at the same time. The bombarded leaf tissue may be regenerated under selection on sucrose-reduced medium (antibiotic free) under strong light. Transformants which display a normal green phenotype and are able to grow photoautotrophically may be selected.

Embodiment 4: Method for the Selection of Plastid Transformants Based on the Inactivation and Restoration of the petA Gene, Whereby Inactivation Mutants are Selected by a Novel Procedure This procedure may be used with all mutants that are photosynthesis defective. Similar to embodiment 3, selection of plastid transformants may be based on the inactivation and restoration of the petA gene. In contrast, the selection for ΔpetA mutants may be carried out on medium containing a herbicide that requires active photosynthesis for efficacy, e.g. the herbicide Paraquat. Any complete inactivation of the petA gene may result in an increased resistance of the mutant plant line to such a herbicide compared to wild-type. Importantly, the introduction of any antibiotic or herbicide resistance marker during the first transformation step can be omitted.

Vectors of this Invention Provide the Possibility to Introduce Novel Functions During the First or the Second Transformation Step Genes or sequences of interest may be introduced during the first or the second step of transformation or during both. Therefore, multiple genes or functional operons may be introduced into the target plant. Among others, this is of particular interest for the generation of new metabolic pathways in transplastomic plants, as a significant number of novel genes and/or regulation factors may have to be integrated into the plastome.

Similarly, desired sequences may be introduced or removed e.g. in order to manipulate plastid gene expression pattern.

Vectors of this Invention Provide the Possibility to Reuse Selection Markers

A further application of the two step strategy described in this invention is the possibility to reuse the same selection marker for another transformation after removing it from the genome during the second step. Subsequently, it may be removed again and the process may be repeated. This provides means for the insertion of a potentially unlimited number of genes or functional operons into the plastid genome using the same marker gene. This is an important step towards overcoming the shortage of selection markers for plastid gene transformation.

Vectors of this Invention Allow the Introduction of Sequences of Interest at Independent Loci By using various combinations of the described methods (e.g. embodiment 1, 2 and 3 using rpoA, ycf3 and petA, respectively, as target sites), the genes of interest can be introduced into different target sites of the plastome. The method described here will also function using inactivation and restoration of other photosynthesis related target genes, such as e.g. psbA. Consequently numerous potential target sites exist. Using homologous recombination, novel functions may also be introduced at sites independent of marker genes.

Vectors of this Invention Provide Novel Selection Schemes

The aadA gene is the only selectable marker gene that is used routinely (Heifetz, 2000), and the nptII gene conferring resistance to kanamycin is the only alternative that has been shown to function in higher plant plastid transformation (Carrer et al., 1993). The vectors of this invention overcome the shortage of selectable marker genes. Novel selection inhibitors for plastid transformation that are described here include paraquat, morphamquat, diquat, difenzoquat and cyperquat. These substances belong to the group of photosystem I acceptor herbicides (Hock & Elsner, 1995). They are not inhibitors of photosystem 1, but they are reduced by photosystem I instead of ferredoxin and NADP. Autooxidation of reduced inhibitors then produces oxygen radicals which are highly toxic. The toxicity of these herbicides therefore depends on light and oxygen.

If the electron transport through photosystem I is interrupted either by deletion of an essential gene of photosystem I or of the cytochrome b/f complex (for example petA) these mutant plants are more resistant to photosystem I acceptor herbicides like paraquat than wild-type plants. Such herbicides may therefore be suitable selection agents for the knock out of these genes. Any albino will be insensitive to these inhibitors; thus any disruption that leads to photosynthesis deficiency could be selected for this way.

In one embodiment of the invention, step (d) may be assisted by inhibitor resistance. Inhibitor resistance may be achieved via stable or transient introduction of an inhibitor or antibiotic resistance in step (c). Preferably, an inhibitor resistance introduced in step (c) is transient in order to allow the generation of selection marker free transplastomic plants as an end result. An inhibitor resistance gene may be removed by methods known in the art, e.g. as described by Fischer et al. (1996) or by Iamtham and Day (2000). Further, an inhibitor or antibiotic may be applied only initially in step (d) similarly as described above for step (b). Omitting the inhibitor at a later stage allows loss of a resistance gene introduced in step (c). This embodiment takes advantage of the regeneration of a discernible phenotype in steps (c) and (d) according to the principles of the invention, but the achievement of a homoplasmic state in step (d) may be made more efficient.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel et al., 1999, Maniatis et al., 1989 and Silhavy et al., 1984.

Example 1

Construction of a Selection System Based on the Inactivation of the rpoB Gene

Construction of Transformation Vector pIC571 for the Inactivation of the rpoB Gene Leaves of tobacco plants were ground under liquid nitrogen and total DNA (*Nicotiana tabacum* L. var. *petit havanna*) was isolated using the Qiagen "DNeasy Plant Mini Kit".

Using this total genomic DNA as a template the region of the tobacco chloroplast genome containing the rpoB and trnA7 genes was amplified by PCR. The following pair of oligonucleotide primers was used: p38 5'-AAG ATG AAC CTG TTC CCA TG-3' (SEQ ID NO:1) (annealing with plastome nucleotides 25967–25986; position numbers according to GenBank accession number Z00044.1) and p39 5'-CAC TTC TTC CCC ACA CTA CG-3' (SEQ ID NO:2) (annealing with plastome nucleotides 29616–29597). The PCR amplification using Taq-polymerase (Sigma) was performed as follows: 60 sec at 95° C., 1 cycle; 30 sec at 94° C., 60 sec at 55° C., 240 sec at 72° C., 32 cycles; final extension at 72° C. for 10 min. The reaction products were analyzed by agarose gel electrophoresis. Only a single fragment could be detected. It showed the expected size of 3.65 kbp. The fragment was ligated into vector pCR11 (Invitrogen) according to the protocol of the supplier, yielding plasmid pCR rpoB01. The identity of the plasmid insert was verified by sequencing (Toplab; Munich).

To inactivate the plastid rpoB-Operon, a selectable aadA marker cassette should replace the 5'-upstream region and the translation start of rpoB, represented by a 699 bp Ava I fragment (plastome postion 27508–28206). As a prerequisite, an additional Ava I restriction site in the multiple cloning site of plasmid pCR rpo01 had to be removed. This was done by cutting the plasmid with the enzyme Xho I, followed by a fill-in reaction using Klenow polymerase and nucleotides. The linear fragment was then religated and transformed into bacteria. As a consequence the resulting plasmid pCR rpoB ΔXho only contained the two Ava I sites mentioned above.

Plasmid pCR rpoB ΔXho was digested with Ava I. The larger of the two resulting fragments (6861 bp and 699 bp) was purified from an agarose gel using the Qiagen gel extraction kit. The resulting sticky ends of the 6861 bp fragment created by the Ava I treatment were converted into blunt ends using Klenow enzyme and nucleotides. The resulting DNA was treated with calf alkaline phosphatase (Roche Diagnostics GmbH, Mannheim, Germany) to suppress self ligation in the following step.

Finally, a 1412 bp Sma I fragment containing the aadA expression cassette from vector pUC16SaadA-Sma (Koop et al., 1996) was ligated into the 6861 bp Ava I fragment. The ligation products were transformed into bacteria. The plasmids of the resulting bacterial clones were analyzed for the presence and the orientation of the aadA-insert. 7 positive clones showed insertion of the aadA-cassette in sense direction compared to the rpoB gene. The plasmid was designated pIC571 (pCR rpoB aadA-I) (FIG. 1). Large amounts of pCR rpoB aadA-I plasmid DNA were isolated using the Qiagen Plasmid Maxiprep kit.

Primary Transformation and Selection of Homoplastomic ΔrpoB Mutants

PEG mediated transmembrane DNA transfer into protoplasts is a reproducible method for plastid transformation of higher plants (Golds et al., 1993; O'Neill et al., 1993). Protoplast regeneration was recently optimized according to Dovzhenko et al., 1998.

A. Protoplast isolation: Leaves from about 3 weeks old tobacco plants (Nicotiana tabacum cv. petit Havanna) were cut to 1 mm stripes and incubated overnight with 0.25% cellulase R10 and 0.25% macerozyme R10 (Yakult, Honsha Japan) dissolved in F-PIN medium. Following standard filtration, flotation and sedimentation procedures (Koop et al., 1996) protoplasts were resuspended in transformation medium, the total number of protoplasts was determined, and the density was adjusted to $5 \times 10^6$ protoplasts per ml.

F-PIN medium (pH 5.8 (KOH), osmolarity: 550 mOsm): $KNO_3$ (1012 μg/ml), $CaCl_2.2H_2O$ (440 μg/ml), $MgSO_4.7H_2O$ (370 μg/ml), $KH_2PO_4$ (170 μg/ml), $NH_4$-succinate (10 ml of 2M stock), EDTA-Fe(III) Na-salt (40 μg/ml), KJ (0.75 μg/ml), $H_3BO_3$ (3 μg/ml), $MnSO_4.H_2O$ (10 μg/ml), $ZnSO_4.7H_2O$ (2 μg/ml), $Na_2MoO_4.2H_2O$ (0.25 μg/ml), $CuSO_4.5H_2O$ (0.025 μg/ml), $CoCl_2.6H_2O$ (0.025 μg/ml), inositol (200 μg/ml), pyridoxin-HCl (2 μg/ml), thiamin-HCl (1 μg/ml), biotin (0.02 μg/ml), nicotinic acid (2 μg/ml), BAP (1 μg/ml), NAA (0.1 μg/ml), Polypuffer 74 (10 ml), sucrose (~130 000 μg/ml).

Transformation medium (pH 5.8 (KOH), osmolarity: 550 mOsm): $MgCl_2.6H_2O$ (3050 μg/ml), MES (1000 μg/ml), mannitol (~80000 μg/ml).

B. Plastid transformation and protoplast embedding: 50 μg DNA (transformation vector pIC571), 7 μl F-PCN, and 100 μl (500,000 cells) of protoplast suspension were added to 125 μl 40% PEG solution, mixed carefully and incubated for 7.5 min. Another 125 μl of F-PCN were added, mixed and incubated for 2 min. The volume was filled up to 3 ml (with F-PCN) and 3 ml of F-alginate medium was added. Alginate embedding in thin layers is performed by applying 625 μl of protoplast-alginate mixture to polypropylene grids laying on the surface of $Ca^{2+}$-medium. After solidification grids were removed and placed upside down into liquid F-PCN medium for equilibration (2×10 ml, 30 min each) and then transferred to a new petri dish with 2 ml F-PCN. The embedded protoplasts were incubated in the darkness for the initial 20 hours, followed by a usual 16 h day/8 h dark cycle.

F-PCN medium (pH 5.8 (KOH), osmolarity: 550 mOsm): $KNO_3$ (1012 μg/ml), $CaCl_2.2H_2O$ (440 μg/ml), $MgSO_4.7H_2O$ (370 μg/ml), $KH_2PO_4$ (170 μg/ml), $NH_4$-succinate (10 ml of 2M stock), EDTA-Fe(III) Na-salt (40 μg/ml), KJ (0.75 μg/ml), $H_3BO_3$ (3 μg/ml), $MnSO_4.H_2O$ (10 μg/ml), $ZnSO_4.7H_2O$ (2 μg/ml), $Na_2MoO_4.2H_2O$ (0.25 μg/ml), $CuSO_4.5H_2O$ (0.025 μg/ml), $CoCl_2.6H_2O$ (0.025 μg/ml), inositol (200 μg/ml), pyridoxin-HCl (2 μg/ml), thiamin-HCl (1 μg/ml), biotin (0.02 μg/ml), nicotinic acid (2 μg/ml), BAP (1 μg/ml), NAA (0.1 μg/ml), Polypuffer 74 (10 ml), sucrose (~20 000 μg/ml), glucose (65 000 μg/ml).

F-alginate medium (pH 5.8 (KOH), osmolarity: 550 mOsm): MES (1370 μg/ml), $MgSO_4.7H_2O$ (2500 μg/ml), $MgCl_2.6H_2O$ (2040 μg/ml), mannitol (~77000 μg/ml), alginate (24000 μg/ml).

$Ca^{2+}$-medium (pH 5.8 (KOH), osmolarity: 550 mOsm): MES (1950 μg/ml), $CaCl_2.2H_2O$ (2940 μg/ml), mannitol (~82000 μg/ml), agar, purified (10000 μg/ml).

One week after transformation embedded protoplasts were transferred to solid RMOP medium (see example 3) containing 500 μg/ml spectinomycin and streptomycin each. Every 3 weeks the grids were transferred to fresh medium until no further regenerates appeared. First green regenerates appeared after 5 weeks and were transferred to single petri dishes. As expected, primary ΔrpoB transformants displayed spectinomycin-resistance and a green phenotype in the light while still being heteroplastomic. In order to amplify transformed plastid DNA molecules and to eliminate wild-type genomes, the transformant colonies were transferred to RMOP medium without inhibitors. White sectors appeared after 3 to 5 weeks of culture. Material from white sectors was further subcultured on non-selective medium and subjected to 5 further cycles of regeneration in order to obtain homoplastomic mutant transformants. The resulting lines showed a white phenotype. The transplastomic lines were rooted and propagated on solid VBW-medium (see examples) to obtain mutant plant material for the secondary transformation.

Analysis by PCR and Southern Blotting

Leaves of the mutant ΔrpoB transplastomic plants were ground under liquid nitrogen and total DNA (Nicotiana tabacum L. var. petit havanna) was isolated using the Qiagen "DNeasy Plant Mini Kit".

Plastid transformants were analyzed by PCR amplification. Total DNA isolated from regenerates of several independent lines were used as templates for separate PCR reactions. Two sets of oligonucleotide primers were used to analyze the transplastomic plants. oFCH59 5'-TGC TGG CCG TAC ATT TGT ACG-3' (SEQ ID NO:3) (derived from the 5' portion of the aadA coding region) and oFCH60 5'-CAC TAC ATT TCG CTC ATC GCC-3' (SEQ ID NO:4) (derived from the 3' portion of the aadA coding region) were used to detect the presence of the aadA gene. p42 5'-ATT TGT AGT AGA AGG TAA TTG C-3' (SEQ ID NO:5)

(annealing with plastome nucleotides 29081–29102) and oFCH60 were used to detect correct integration of the aadA gene.

Additional proof of correct integration and the homoplastomic genotype was given by DNA gel blot analysis. Genomic DNAs isolated from sterile grown plants were used for DNA gel blot analysis. The detailed procedure was as follows: 3 μg of total plant DNA per analyzed plant were digested with the appropriate restriction enzyme and separated on a TAE agarose gel (0.8%). The DNA was denatured and transferred onto a positively charged nylon membrane (Hybond-N+, Amersham) as described in Ausubel et al. (1999). The filter was hybridized with digoxigenin-labeled probes in DIG Easy Hyb Buffer (Roche Diagnostics GmbH, Mannheim, Germany), and hybridization signals were detected using the DIG Luminescent Detection Kit (Roche). The membrane was exposed to an X-OMAT LS film at room temperature for 75 minutes. For preparation of a hybridization probe, a 398 bp Sma I/Hind III fragment was excised from plasmid pCR rpoB01, purified from a agarose gel and labeled using the Dig probe labeling kit (Roche).

Construction of Transformation Vector pIC554 for Reconstitution of the rpoB Gene For a proof of principle of the selection system, a transformation vector was constructed, which reconstitutes the deletion of the rpoB regulatory region and introduces a marker restriction site at the same time. The additional marker restriction site should allow to differentiate between recombinant plastome fragments in the respective area and a potential selection of residual wildtype plastome copies (in case the mutant lines were not completely homplastomic).

Plasmid pIC571 (pCR rpoB01) was cut with Xma I. The ends of the linear fragment were converted into a blunt form using Klenow polymerase and nucleotides. The resulting DNA was religated and transformed into bacteria. Plasmids of the bacterial clones were screened for the absence of the Sma I restriction site. DNA from the resulting plasmid pIC554 (pCR rpoB01-ΔSma) (FIG. 2) was isolated for plastid transformation.

The Sma I restriction site of plasmid pIC571 enables easy one step integration of any foreign gene to be expressed in plastids.

Plastid Transformation of ΔrpoB Mutant Lines and Selection of Homoplastomic Lines The goal of the second transformation is to reconstitute the rpoB gene's regulatory region (including the translation start), remove the aadA-cassette and introduce a marker restriction site at the same time. Young leaves from sterile homoplastomic ΔrpoB mutants grown on VBW-medium were bombarded with plasmid pIC554 coated gold particles using the Bio-Rad (Hercules, Calif., USA) PDS-1000/He Biolistic particle delivery system (for detailed procedure see example 3). Two days after bombardment, leaves were cut into small pieces (ca. 3×3 mm) and transferred to solid sucrose-reduced-RMOP medium (containing 3 g/liter sucrose). Every three weeks the leaf pieces were cut again and transferred to fresh medium until no further regenerates appeared. The transformants which display green phenotype and are able to grow photoautotrophically were selected and subjected to several additional rounds of regeneration on sucrose-reduced-RMOP medium to obtain homoplastomic tissue. Homoplastomic transplastomic lines were rooted and propagated on solid B5-medium.

Molecular Analysis of the Secondary Transplastomic Plants

Total DNA isolated from sterile grown plants recovered from the secondary transformation was used for DNA gel blot analysis.

The detailed procedure was as follows: 3 μg of total plant DNA per analyzed plant were digested with restriction enzymes Bam HI and Sma I at the same time and separated on a TAE agarose gel (0.8%). The DNA was denatured and transferred onto a positively charged nylon membrane (Hybond-N+, Amersham) as described in Ausubel et al. (1999). The filter was hybridized with digoxigenin-labeled probes in DIG Easy Hyb Buffer (Roche Diagnostics GmbH, Mannheim, Germany), and hybridization signals were detected using the DIG Luminescent Detection Kit (Roche). The membrane was exposed to an X-OMAT LS film at room temperature for 75 minutes.

For preparation of a hybridization probe, a 398 bp Sma I/Hind III fragment was excised from plasmid pCR rpoB01, purified from an agarose gel and labeled using the Dig probe labeling kit (Roche). This probe should result in a signal of 3629 bp from the secondary transformed plastomes. This is a clear evidence, that the recombinant fragment from the transformation vector has been integrated, as a potentially wild type derived band would have a size of only 1628 bp. The presence of the 3629 bp fragment also indicates the removal of the aadA marker cassette.

To confirm the removal of the aadA marker a second hybridization of the blot (of which the former probe had been removed by a stripping procedure) was done using a 480 bp fragment of the aadA-gene as probe. For probe generation primers oFCH59 and oFCH60 (see above) were used in a PCR Dig labeling reaction according to the protocol of the supplier (Roche).

Example 2

Construction of a Selection System Based on the Inactivation of the rpoA Gene

Construction of Transformation Vector pGEM-rpoA-del for the Inactivation of the rpoA Gene The region of the tobacco chloroplast genome (corresponding to plastome nucleotides 79401–82470) containing the rpoA reading frame was amplified from genomic DNA isolated from leaf tissue of tobacco by PCR using Taq-polymerase (Qiagen, Hilden, Germany). The following pair of oligonucleotide primers was used: p78 5'-Sph I-TTA GTA ACA AGC AAA CCT TG-3' (SEQ ID NO:6) (annealing with plastome nucleotides 79401–79420), and p77 5'-Sma I-TAA TTA CTG AAT CGC TTC CCA-3' (SEQ ID NO:7) (annealing with plastome nucleotides 82470–82450).

The PCR program used was as follows: 2 min at 94° C., 1 cycle; 45 sec at 94° C., 45 sec at 55° C., 2 min at 72° C., 30 cycles; final extention at 72° C. for 10 min. The fragment was ligated into the pGEM-T vector (Promega). The complete rpoA coding region (corresponding to plastome nucleotides 80455–81468) was subsequently deleted by digestion with Dra I and Sca I. A chimeric aadA gene was excised from pUC16SaadA (for a detailed description of pUC16SaadA see Koop et al., 1996) as a Sma I fragment and inserted to replace rpoA and to facilitate selection of chlorolast transformations. A plasmid clone carrying the aadA gene in the opposite orientation as rpoA yielded transformation vector pGEM-rpoA-del (FIG. 3). The identity of the plasmid insert was verified by sequencing (MWG, Munich).

Primary Transformation and Selection of Homoplastomic ΔrpoA Mutants

Young leaves from sterile tobacco plants (cultivation see example 1) were bombarded with plasmid pGEM-rpoA-del coated gold particles using the Bio-Rad (Hercules, Calif., USA) PDS-1000/He Biolistic particle delivery system (detailed procedure see example 3). Two days after bombardment, leaves were cut into small pieces (ca. 3×3 mm) and transferred to solid RMOP-medium containing 500 μg/ml spectinomycin. Leaf pieces were cut again and transferred to fresh medium after 2 weeks, then every 3 weeks until no further regenerants appeared. Primary ΔrpoA transformants displayed spectinomycin-resistance and a green phenotype in the light while still being heteroplastomic. In order to amplify transformed plastid DNA molecules and to eliminate wild-type genomes, the primary transformants were subjected to 3 additional rounds of regeneration on selective medium. Since segregation leads to the occurrence of white and green sectors, material from white sectors was subjected to several additional rounds of regeneration on non-selective medium in order to obtain homoplastomic mutant transformants. Homoplastomic transformed lines were rooted and propagated on solid VBW-medium (Aviv and Galun, 1985; see example 1).

Molecular Analysis of Potential Plastid Transformants by Southern Analysis

3 μg of total plant DNA per analysed plant were digested with the appropriate restriction enzyme and separated on a TBE-agarose gel (0.8%). The DNA was denatured and transferred to a positively charged nylon membrane (Hybond-N+, Amersham) as described in Ausubel et al., 1999. The filter was hybridised with digoxigenin-labeled probes in DIG Easy Hyb Buffer (Roche Diagnostics GmbH, Mannheim, Germany), and hybridisation signals were detected using the DIG Luminescent Detection Kit (Roche). The membrane was exposed to a X-OMAT LS film at room temperature.

A fragment suitable for discrimination between wild type and transformed plastome was gel purified using the QIAquick Gel Extraction Kit (QIAgen, Hilden, Germany), labelled with digoxigenin using the Roche DIG DNA Labelling Kit and used for hybridisation.

Construction of the Transformation Vector for Reconstitution of the rpoA Gene

For a demonstration, that any gene of interest may be inserted using the described selection system, a transformation vector was constructed, which reconstitutes the deletion of the rpoA coding region and introduces a gus marker gene at the same time.

This vector contains the rpoA coding region and the gus gene, flanked by 5'-and 3'-homologous sequences which were amplified from the tobacco chloroplast genome by PCR using the following two pairs of primers: oFCH112 5'-Nco I-TAC TAT TAT TTG ATT AGA TC-3' (SEQ ID NO:8) (annealing with plastome nucleotides 81471–81490), oFCH113 5'-Sma I-TAA TTA CTG AAT CGC TTC CCA-3' (SEQ ID NO:9) (annealing with plastome nucleotides 82470–82450), and oFCH114 5'-Sph I-TTA GTA ACA AGC AAA CCT TG-3' (SEQ ID NO:10) (annealing with plastome nucleotides 79401–79420), oFCH137 5'-Pst I-ATC ACT AGT TGT AGG GAG GGA TCC ATG GTT CGA GAG AAA GTA AC-3' (SEQ ID NO:11) (annealing with plastome nucleotides 81468–81449). The amplified 5'-homologous fragment (corresponding to plastome nucleotides 81471–82470) contains 1000 nucleotides upstream of the rpoA start codon. The amplified 3'-homologous fragment (corresponding to plastome nucleotides 79401–81468) contains a ribosome binding site (RBS), the rpoA coding region, and 1054 nucleotides downstream of the rpoA stop codon. The 5' and 3'-homologous fragments are subcloned into plasmid pUC16SRBSuidA3'rbcL (Koop et al., 1996), regenerating transformation vector pIC598. The construction of this vector is shown in FIG. 4. The identity of the plasmid insert was verified by sequencing (MWG, Munich).

Plastid Transformation of ΔrpoA Mutant Lines and Selection of Homoplastomic Lines The goal of the second transformation is to reconstitute the rpoA coding region, remove the aadA-cassette and introduce the gus marker gene at the same time. Young leaves from sterile homoplastomic ΔrpoA mutants grown on VBW-medium were bombarded with plasmid pIC598-coated gold particles using the Bio-Rad (Hercules, Calif., USA) PDS-1000/He Biolistic particle delivery system (detailed procedure see example 3). Two days after bombardment, leaves were cut into small pieces (ca. 3×3 mm) and transferred to solid sucrose-reduced-RMOP medium (containing 3 g/liter sucrose). Every three weeks the leaf pieces were cut again and transferred to fresh medium until no further regenerates appeared. Transformants which display green phenotype and are able to grow photoautotrophically were selected and subjected to several additional rounds of regeneration on sucrose-reduced-RMOP medium to obtain homoplastomic tissue. Homoplastomic transplastomic lines were rooted and propagated on solid B5-medium.

Molecular Analysis of Potential Plastid Transformants by Southern Analysis

3 μg of total plant DNA per analysed plant were digested with the appropriate restriction enzyme and separated on a TBE-agarose gel (0.8%). The DNA was denatured and transferred to a positively charged nylon membrane (Hybond-N+, Amersham) as described in Ausubel et al., 1999. The filter was hybridised with digoxigenin-labelled probes in DIG Easy Hyb Buffer (Roche Diagnostics GmbH, Mannheim, Germany), and hybridisation signals were detected using the DIG Luminescent Detection Kit (Roche). The membrane was exposed to an X-OMAT LS film at room temperature.

A fragment suitable for discrimination between wild type and transformed plastome was gel purified using the QIAquick Gel Extraction Kit (QIAgen, Hilden, Germany), labelled with digoxigenin using the Roche DIG DNA Labelling Kit and used for hybridisation.

Example 3

Construction of a White/Green Selection System Based on Inactivation of the ycf3 Gene Construction of Transformation Vector pIC553 for Targeted Inactivation of the ycf3

The region of the tobacco chloroplast genome containing the ycf3 reading frame was amplified from genomic DNA isolated from leaf tissue of tobacco by PCR using Taq-polymerase (Qiagen). The following pair of oligonucleotide primers was used: oFCH63 (5'-GAA GTT TCT TTC TTT GCT ACA GC-3' (SEQ ID NO:12), annealing with plastome nucleotides 45033–45053) and oFCH64 (5'-GM TTA CCA AAC CAT TTG ACC C-3' (SEQ ID NO:13) annealing with plastome nucleotides 47667–47647).

The PCR program used was as follows: 2 min at 94° C., 1 cycle; 45 sec at 94° C., 45 sec at 55° C., 2 min at 72° C., 30 cycles; final extention at 72° C. for 10 min. The fragment was ligated into the pGEM-T vector (Promega), regenerating plasmid pIC517. The first exon and 5' regulatory element of ycf3 was subsequently deleted by digestion with Bbr PI and Bst 11071. Bst 11071 cuts 373 nucleotides upstream of the ycf3 start codon (nucleotide position 46266). The Bbr PI site is located within intron 1 of ycf3 (close to the end of the first exon). A chimeric aadA gene was excised from pUC16SaadA (for a detailed description of pUC16SaadA see Koop et al., 1996) as a Sma I fragment. It was inserted to replace ycf3 and to facilitate selection of plastid transformants. A plasmid clone carrying the aadA gene in the opposite orientation as ycf3 yielded transformation vector pIC553 (FIG. 5). The identity of the plasmid insert was verified by sequencing (MWG, Munich).

Electrotransformation of E. coli Cells

Preparation of electrocompetent cells: 1 liter of LB-medium (1% (w/v) casein hydrolysate, 0.5% (w/v) yeast extract, 0.5% (w/v) NaCl) is inoculated 1:100 with fresh overnight culture of E. coli JM109 cells (Promega, Madison, Wis., USA). The cells are grown at 37° C. with shaking at 220 rpm to an optical density of 0.5 at 600 nm. The cells are chilled on ice for 20 min and centrifuged for 15 min (4000 rpm, 4° C.). The supernatant is removed and the pellet is resuspended in 1 liter of ice-cold sterile 10% (v/v) glycerol. The cells are centrifuged two times as described before, resuspending the cells in 500 ml and 20 ml of ice-cold sterile 10% (v/v) glycerol, respectively. The cells are centrifuged an additional time and the pellet is resuspended in 2 ml of ice-cold sterile 10% (v/v) glycerol. This suspension is frozen in aliquots of 80 µl and stored at −80° C.

Electrotransformation using the Bio-Rad (Hercules, Calif., USA) Micro Pulser electroporation apparatus: The electrocompetent cells are thawed on ice. 40 µl of the cell suspension are mixed with 2 µl of the ligation mixture and transferred into a prechilled, sterile 0.2 cm cuvette (Bio-Rad). The suspension is shaken to the bottom and the cuvette is placed into the chamber slide. The chamber slide is pushed into the chamber and the cells are pulsed at 2.5 kV. The cuvette is removed from the chamber and the cells are suspended in 1 ml of SOC-medium (2% (w/v) casein hydrolysate, 0.5% (w/v) yeast extract, 10 mM NaCl, 2.5 mM KCl, 10 mM $MgCl_2$ and 20 mM glucose). The suspension is shaken for 1 h at 37° C. and 100 µl of the suspension is plated on LB plates containing 150 mg/l ampicillin.

Primary Transformation and Selection of Homoplastomic Δycf3 Mutants

Tobacco seeds (Nicotiana tabacum cv. petit havanna) were surface sterilized (1 min in 70% ethanol, 10 min in 5% Dimanin C, Bayer, Leverkusen, Germany), washed 3 times for 10 min in sterile $H_2O$ and put on B5 medium (preparation see below). Plants were grown at 25° C. in a 16 h light/8 h dark cycle (0.5–1 W/m$^2$, Osram L85W/25 Universal-White fluorescent lamps).

6 leaves from 4 weeks old, sterile grown Nicotiana tabacum L. var. petit havanna plants were cut and transferred on RMOP-medium (preparation see below). 35 µl of a gold suspension (0.6 micron, Biorad, München; 60 mg/ml ethanol) was transferred into a sterile Eppendorf-cup (Treff, Fisher Scientific, Ingolstadt, Germany), collected by centrifugation and washed with 1 ml sterile $H_2O$. The gold pellet was resuspended in 230 µl sterile $H_2O$, 250 µl 2.5 M $CaCl_2$ and 25 µg DNA (transformation vector pIC553) were added. After thoroughly resuspending the mixture, 50 µl 0.1 M spermidin were added, mixed and incubated for 10 min on ice. Then the gold was collected by centrifugation (1 min, 10000 rpm) and washed twice with 600 µl ethanol (100%, p.A.). The gold was collected by centrifugation (1 min, 10000 rpm) and finally resuspended in 72 µl ethanol (100%, p.A.). A macrocarrier was inserted in the macrocarrier holder and 5.4 µl of the gold-suspension were applied. The bombardment was carried out with a Bio-Rad (Hercules, Calif., USA) PDS-1000/He Biolistic particle delivery system using the following parameters:

rupture disc 900 psi
helium pressure 1100 psi
vacuum 26–27 inches Hg
macrocarrier at the top level
leaf piece at the third level 6 leaf pieces were bombarded each with 5.4 µl gold-suspension. After bombardment the leaf pieces were incubated for 2 days at 25° C. on RMOP-medium.

Two days after bombardment, leaves were cut into small pieces (ca. 3×3 mm) and transferred to solid RMOP-medium containing 500 µg/ml spectinomycin. Leaf pieces were cut again and transferred to fresh medium after 2 weeks, then every 3 weeks until no further regenerates appeared. Primary Δycf transformants displayed spectinomycin-resistance and a green phenotype in the light while still being heteroplastomic. In order to amplify transformed plastid DNA molecules and to eliminate wild-type genomes, the primary transformants were subjected to 3 additional rounds of regeneration on selective medium. Since segregation leads to the occurrence of white, mixed and green sectors, material from white sectors was subjected to several additional rounds of regeneration on non-selective medium in order to obtain homoplastomic mutant transformants. Homoplastomic transformed lines were rooted and propagated on solid VBW-medium (Aviv and Galun, 1985) (preparation see below) under low light condition to obtain wild-type-similar Δycf3 mutants (display light green phenotype).

RMOP (pH5.8 with KOH): $NH_4NO_3$(1650 µg/ml), $KNO_3$ (1900 µg/ml), $CaCl_2\times2H_2O$ 440 (µg/ml), $MgSO_4\times7H_2O$ (370 µg/ml), $KH_2PO4$ (170 µg/ml), EDTA-Fe(III)Na (40 µg/ml), KI (0.83 µg/ml), $H_3BO_3$ (6.2 µg/ml), $MnSO_4\times H_2O$ (22.3 µg/ml), $ZnSO_4\times7H_2O$ (8.6 µg/ml), $Na_2MoO_4\times2H_2O$ (0.25 µg/ml), $CuSO_4\times5H_2O$ (0.025 µg/ml), $CoCl_2\times6H_2O$ (0.025 µg/ml), Inositol (100 µg/ml), Thiamine-HCl (1 µg/ml), Benzylaminopurine (1 µg/ml), Naphthalene acetic acid (0.1 µg/ml), Sucrose (30000 µg/ml), Agar, purified (8000 µg/ml).

B5 (pH5.7 with KOH): $KNO_3$ (2500 µg/ml), $CaCl_2\times2H_2O$ (150 µg/ml), $MgSO_4\times7H_2O$ (250 µg/ml), $NaH_2PO_4\times H_2O$ (150 µg/ml), $(NH_4)_2SO_4$ (134 µg/ml), EDTA-Fe(III)Na (40 µg/ml), KI (0.75 µg/ml), $H_3BO_3$ (3 µg/ml), $MnSO_4\times H_2O$ (10 µg/ml), $ZnSO_4\times7H_2O$ (2 µg/ml), $Na_2MoO_4\times2H_2O$ (0.25 µg/ml), $CuSO_4\times5H_2O$ (0.025 µg/ml), $CoCl_2\times6H_2O$ (0.025 µg/ml), Inositol (100 µg/ml), Pyridoxine-HCl (1 µg/ml), Thiamine-HCl (10 µg/ml), Nicotinic acid (1 µg/ml), Sucrose (20000 µg/ml), Agar, purified (7000 µg/ml).

VBW (pH5.8 with KOH): $NH_4NO_3$(1650 µg/ml), $KNO_3$ 1900 (µg/ml), $CaCl_2\times2H_2O$ (440 µg/ml), $MgSO_4\times7H_2O$ (370 µg/ml), $KH_2PO_4$ (170 µg/ml), EDTA-Fe(III)Na (40 µg/ml), KI (0.83 µg/ml), $H_3BO_3$(6.2 µg/ml), $MnSO_4\times H_2O$ (22.3 µg/ml), $ZnSO_4\times7H_2O$ (8.6 µg/ml), $Na_2MoO_4\times2H_2O$ (0.25 µg/ml), $CuSO_4\times5H_2O$ (0.025 µg/ml), $CoCl_2\times6H_2O$ (0.025 µg/ml), Inositol (100 µg/ml), Pyridoxin-HCL (0.5 µg/ml), Thiamine-HCl (1 µg/ml), Glycine (2 µg/ml), Nicotinic acid (0.5 µg/ml), Indolylacetic acid (2 µg/ml), Kinetin (0.2 µg/ml), Sucrose (30000 µg/ml), Caseinhydrolysat (500 µg/ml), Agar, purified (7000 µg/ml).

Analysis by PCR and Southern Blotting

Plastid transformants were identified by PCR amplification. Total DNA isolated from the first regenerates of 40 independent lines were used as templates for separate PCR reactions. The method used was as follows: 100 mg fresh leaf tissues of tobacco were disrupted (2×1 min at 25 Hz) in 200 µl AP1 buffer (DNeasy plant mini kit, QIAGEN)/1 µl reagent DX (foaming inhibition, QIAGEN) using mixer mill MM 300 (Retsch) in a 1.5 ml microcentrifuge tube with one 3 mm tungsten carbide bead. DNA was then purified using the DNeasy plant mini kit. Five sets of primers (sequences are shown in table 1), namely oFCH59 and oFCH60; oFCH52 and oFCH53; oFCH52 and oFCH60; oFCH53 and oFCH59; oFCH60 and oFCH27 were employed to analyze transplastomic plants. oFCH52 and oFCH53 should result in an amplification product of 900 bp from the wild-type plastome and a product of 1700 bp from transformed plastomes, whereas oFCH59 and oFCH60 should result in an amplification product of 480 bp from the transformed plants and no product from wild-type. Likewise, oFCH52, oFCH60 and oFCH53, oFCH59 should only amplify a product of 867 bp and 1368 bp from the transformed plants, respectively. The combination of oFCH60 and oFCH27 can determine whether the transformants carry correct insertions or not by amplifying a product of 2541 bp from correctly transformed plastomes.

as follows: 2 min at 94° C., 1 cycle; 30 sec at 94° C., 30 sec at 55° C., 1 min at 72° C., 35 cycles; final extension at 72° C. for 10 min. The amplified fragment was gel purified using the QIAquick Gel Extraction Kit Qiggen, Hilden, Germany) and then used for hybridization. This probe should result in a signal of 2998 bp from the transformed plastomes and a signal of 2198 bp from wild-type plastomes. The result showed that no wild-type plastid DNA could be detected in all 10 examined mutant lines.

Construction of Transformation Vector pIC526 for Reconstitution of the ycf3 Gene Transformation vector pIC526 was designed to transform the mutant Dycf3 line with the goal to reconstitute the ycf3 gene, delete the aadA cassette and insert a GFP gene at the same time.

TABLE 1

| Primers | sequences | location |
|---|---|---|
| oFCH59 | 5'-TGC TGG CCG TAC ATT TGT ACG-3' (SEQ ID NO:3) | derived from the 5' portion of the aadA coding region |
| oFOH60 | 5'-CAC TAC ATT TCG CTC ATC GCC-3' (SEQ ID NO:4) | derived from the 3' portion of the aadA coding region |
| oFCH52 | 5'-CAC TAC ATT TCG CTC ATC GCC-3' (SEQ ID NO:14) | annealing with plastome nucleotides 45903-45922, located within cloned plastid DNA fragment |
| oFOH53 | 5'-GAC TAT AGT TAA TGG ATA CTT-3' (SEQ ID NO:15) | annealing with plastome nucleotides 46812-46792, located within cloned plastid DNA fragment |
| oFOH27 | 5'-TGC TCA AGA CTT TAG TGG ATC-3' (SEQ ID NO:16) | annealing with plastome nucleotides 44799-44819, located within chloroplast genome outside of cloned plastid DNA fragment |

PCR results showed that 24 lines of transformants carried the aadA gene with correct insertion in the plastid genome but they were still heteroplastomic in the first cycle of regeneration. The data are also consistent with phenotypic appearance of the respective lines, which indicated that the pigment deficiency was correlated with deletion of ycf3.

Homoplasmy was verified by DNA gel blot analysis. Genomic DNAs isolated from young leaves from plants derived from the fourth cycle of regeneration grown under low light conditions were used for DNA gel blot analysis. The detailed procedure was as follows: 4 μg of total plant DNA per analyzed plant were digested with restriction enzyme Xma JI and separated on a TBE-agarose gel (0.8%). The DNA was denatured and transferred to a positively charged nylon membrane (Hybond-N+, Amersham) as described in Ausubel et al. (1999). The filter was hybridized with digoxigenin-labeled probes in DIG Easy Hyb Buffer (Roche Diagnostics GmbH, Mannheim, Germany), and hybridization signals were detected using the DIG Luminescent Detection Kit (Roche). The membrane was exposed to an X-OMAT LS film at room temperature for 80 minutes.

For preparation of a DIG labeled probe, plasmid pIC522 (see below) was used as template to amplify a 520 bp fragment using the following pair of primers: oFCH69 (5'-CAT TGG AAC TGC TAT GTA GGC-3' (SEQ ID NO:17), corresponding to tobacco plastome sequence 47149–47169) and oFCH64 (5'-GAA TTA CCA AAC CAT TTG ACC C-3' (SEQ ID NO:13), corresponding to tobacco plastome sequence 47667–47647). The PCR DIG Probe Synthesis Kit from Roche was used. The PCR program was The region of the tobacco chloroplast genome containing the first exon and 5' regulatory element of ycf3 (571 bp) was amplified from genomic DNA isolated from leaf tissue of tobacco by PCR. The following pair of oligonucleotide primers was used: oFCH48 5'-Sma I-Dra I-Kpn I-GTG TTT TTC TCC TCG TAA GAC-3' (SEQ ID NO:18) (annealing with plastome nucleotides 46070–46090) and oFCH49 5'-Sma I-Bam HI-Bbr PI-Nhe I-CCG TTA TGT ACA CAA AAT TG-3' (SEQ ID NO:19) (annealing with plastome nucleotides 46637–46618). The PCR program was as follows: 2 min at 94° C., 1 cycle; 45 sec at 94° C., 45 sec at 55° C., 2 min at 72° C., 30 cycles; final extension at 72° C. for 10 min. The fragment was digested with Sma I and ligated into plasmid pIC517 (construction see above) digested with Bbr Pi and Bst 11071. A plasmid clone carrying the first exon and 5' regulatory element of ycf3 in the correct orientation regenerated plasmid pIC522, which contains a cloned plastid DNA with additional 5 restriction sites.

The coding region of GFP was amplified from plasmid pKCZ-GFP (FIG. 6) by PCR using the following pair of primers: oFCH25 (5'-CTA GCT AGC TTA TTT GTA TAG TTC ATC CAT-3' (SEQ ID NO:20) and oFCH26 (5'-TCC CCC GGG GCC GTC GTT CAA TGA GAA TGG-3' (SEQ ID NO:21). The PCR program was as follows: 2 min at 94° C., 1 cycle; 45 sec at 94° C., 45 sec at 55° C., 2 min at 72° C., 30 cycles; final extension at 72° C. for 10 min. The amplified GFP fragment was cut with Sma I and Nhe I, and then ligated into pIC522 cut with Bbr PI and Nhe I, generating pIC526 (FIG. 3). The identity of the plasmid insert was verified by sequencing (MWG, Munich).

Plastid Transformation of Dycf3 Mutant Lines and Selection of Homoplastomic Lines The goal of the second transformation was to reconstitute the ycf3 gene, remove the aadA marker and to introduce the gfp gene at the same time. Young leaves from sterile homoplastomic Dycf3 mutants grown under low light conditions on solid VBW medium were bombarded with plasmid pIC526 coated gold particles using the Bio-Rad (Hercules, Calif., USA) PDS-1000/He Biolistic particle delivery system (detailed procedure see above). Two days after bombardment, leaves were cut into small pieces (ca. 3×3 mm), transferred to solid sucrose-reduced-RMOP medium (containing 3 g/liter sucrose) and cultivated under low light conditions for two weeks. Every three weeks leaf pieces were cut again, transferred to fresh medium and cultivated under strong light conditions until no further regenerates appeared. Transformants, which display a green phenotype and are able to grow photoautotrophically were selected and subjected to several additional rounds of regeneration on sucrose-reduced-RMOP medium to obtain homoplastomic tissue. Homoplastomic transplastomic lines were rooted and propagated on solid B5-medium under strong light condition.

Molecular Analysis of the Secondary Transplastomic Plants

Plastid transformants were identified by PCR amplification. Total DNA isolated from primary transformants which displayed green phenotype and were able to grow photoautotrophically was used as a template for PCR analysis using the following primer pair: oFCH76 (5'-GTA GCA ATC CAT TCT AGA AT-3' (SEQ ID NO:22), annealing with plastome nucleotides 46269–46288) and oFCH53 (5'-GAC TAT AGT TAA TGG ATA CTC-3' (SEQ ID NO:15), annealing with plastome nucleotides 46812–46792). This pair of oligonucleotide primers should result in an amplification product of 540 bp from the wild-type plastome, a product of 1400 bp from plastomes correctly transformed in the second round, and no product from unchanged first round transformants (since the site for p76 annealing was deleted).

Homoplasmy was verified by DNA gel blot analysis. Genomic DNA was isolated from young leaves of plants derived from the fourth cycle of regeneration grown under strong light conditions and digested with Ava I. The probe used was the same as that for Dycf3 mutants (detailed procedures for DNA blotting and hybridization see above). The probe generates a signal of 1212 bp for wild-type plastome, a signal of 2015 bp for plastomes correctly transformed in the second round, and a signal of 6852 bp for unchanged first round transformants.

To confirm the removal of the aadA marker a second hybridization of the blot (of which the former probe had been removed by a stripping procedure) was done using a 480 bp fragment of the aadA-gene as probe. For probe generation primers oFCH59 and oFCH60 (see above) were used in a PCR Dig labeling reaction according to the protocol of the supplier (Roche).

Example 4

Construction of a Selection System Based on the Inactivation of a Photosynthesis Related Gene Construction of Transformation Vector pIC558 for Inactivation of the Plastid Encoded petA Gene All cloning procedures were carried out using standard protocols as described in example 1 and in Ausubel et al., 1999.

Vector pIC558 comprises two flanking sequences derived from the tobacco plastome and an aadA-cassette (pUC16S aadA Sma vollst, Koop et al., 1996) in between. The homologous sequences are 5' and 3' regions of the petA gene, 1 kb each. The aadA-cassette replaces the petA gene (962 bp) and 300 bp of the petA 3' region.

Both flanking fragments were amplified by PCR using the following oligo pairs as primers: oSK13 (5'-GGAATTC-CATATGGTATAAAACTCATGTGTGTAAGAAA-3') (SEQ ID NO:23) and oSK14 (5'-TCCCCCGGGGGTC-CAATCATTGATCGCGAAA-3') (SEQ ID NO:24), generating an Nde I and a Sma I site at the ends, and oSK15 (5'-TTCCCCGGGTTCTAAATAGAAAGA AAGT-CAAATTTG-3') (SEQ ID NO:25) and oSK16 (5'-CATG-CATGCGAATGAATAAGATTCTCTTAGCTC-3') (SEQ ID NO:26), generating a Sma I and a Sph I site at the fragment ends. The PCR program used was as follows: 3 min at 94° C., 1 cycle; 45 sec at 94° C., 45 sec at 55° C., 1.5 min at 72° C., 30 cycles; final extension at 72° C. for 10 min. The digested fragments (left/right flank) and the aadA-cassette as Sma I fragment were cloned in one step into the pUC19 vector which was digested with Nde I and Sph I. Construct pIC558 was analyzed by restriction experiments. The PCR amplified fragments were sequenced to prove the correct sequence of the flanking regions.

Transformation Vector pIC558 is shown in FIGS. 8 and 9.

Construction of Transformation Vector pIC597, pIC599 and pIC600 for Reconstitution of the petA Gene The aim of the second transformation is to cure the petA inactivation and insert a new gene of interest (uidA or aphA-6, potentialy npt II) into the plastome simultaneously. Therefore, the petA gene and a gene cassette (containing 5'/3' regulatory elements) were cloned in between the left/right flanking sequences. Vector pIC597 (uidA-cassette) comprises the same flanking sequences as vector pIC558, the petA gene and the uidA gene-cassette.

A fragment of about 2.2 kb containing 1 kb left flank, the petA gene sequence (962 bp) and 300 bp of the 3' region of the petA gene was amplified by PCR using the following oligo pair as primers: oSK13 (5'-GGAATTCCATATGG-TATAAAACTCATGTGTGTAAGAAA-3') (SEQ ID NO:23) and oSK71 (5'-TCCCCCGGGTAGAAAACTAT-TGATACGTCTTATGG-3'), (SEQ ID NO:27), generating an Nde I and a Sma I site at the fragment ends. The PCR program used was as follows: 3 min at 94° C., 1 cycle; 45 sec at 94° C., 45 sec at 55° C., 3 min at 72° C., 30 cycles; final extension at 72° C. for 10 min. This fragment and the right flank were cloned together into pUC19. This vector pIC651 ('petA+1 kb5'+1,3 kb3") comprises a 1 kb left flank, the petA coding sequence, 300 bp of the 3' region and a 1 kb right flank corresponding to *Nicotiana tabacum* plastome sequence 63.335–66.597.

The new gene of interest (either uidA, Koop et al., 1996; or aphA-6, vector pSK.KmR, Bateman and Purton, 2000; or npt II, Töpfer et al., 1987) was introduced as gene cassette (containing 5'/3' regulatory elements) between both flanking fragments. The uidA-cassette (as Sma I fragment) was taken from vector pIC562 ('pUC16SRBSuidA3'rbcL', Koop et al., 1996). The genes aphA-6 and npt II were cloned into vector pIC562 replacing the uidA-gene, each. After this cloning step the aphA-6-cassette and an npt II-cassette could be isolated by Sma I digestion, respectively. These cassettes were cloned into the petA 3' region (insertions site 300 bp downstream to petA). These vectors are named 'petA-cure-plasmids' (pIC597 with uidA; pIC599 with aph6; pIC600 with nptII).

The constructs were analyzed by restriction experiments and PCR amplified fragments were sequenced to prove the correct sequence of the flanking regions.

A schematic representation of the three vectors is given in FIG. 10. Transformation vector pIC597 is shown in FIG. 11.

Primary Transformation and Selection of Homoplastomic DpetA Mutants.

Plastid transformation by particle gun with vector pIC558 and selection was carried out as described in example 3. PEG mediated plastid transformation with vector pIC558 and selection was carried out as described in example 1.

Secondary Transformation and Selection of Reconstituted Homoplastomic DpetA Mutants.

Plastid transformation by particle gun with vector pIC558 was carried out as described in example 3. PEG mediated plastid transformation with vector pIC588 was carried out as described in example 1. Selection of transformants was done
a) on RMOP medium with reduced sucrose content (0.3%).
   Transformants with a reconstitution of the petA knockout should be able to use photosynthetic energy for growing.
b) on RMOP medium containing kanamycin as selection agent (gene products of aph-6 and nptII detoxify kanamycin).

Transformants showed a decrease of hcf (high chlorophyll fluorescence) during repeated cycles of regeneration.

Analysis of Transformants by PCR and Southern Blotting After Primary Transformation For plant DNA isolation, PCR analysis and Southern blotting standard protocols were used as described in Example 1. For determination of the aadA gene, primers oFCH59aadA480-li and oFCH60-aadA480-re (5'-CAC TAC ATT TCG CTC ATC GCC-3') (SEQ ID NO:4) were used. To determine whether the transformants carry correct insertions, primers oFCH60-aadA480-re and oSK116-petA-re (5'-AAAATAGATTCATTAGTCCGATACC-3') (SEQ ID NO:28) were used. Primer oSK116-petA-re is located upstream (outside) of the 5' flanking fragment. The PCR program used was as follows: 3 min at 94° C., 1 cycle; 45 sec at 94° C., 45 sec at 55° C., 2 min at 72° C., 30 cycles; final extension at 72° C. for 10 min.

First PCR results showed that 12 lines of transformants are carrying the aadA gene with correct insertion in the plastid genome. Further testing and southern analysis to show whether the lines are homoplastomic or heteroplastomic are carried out as described in example 1.

Analysis of Transformants by PCR and Southern Blotting After Secondary Transformation For plant DNA isolation and PCR analysis standard protocols were used as described in example 1. For determination of the uidA gene primers, oSM61-GUS-N (5'-TCACACCGATACCATCAGCG-3') (SEQ ID NO:29) and oSM62-GUS-C (5'-ATTGTTTGCCTCCCTGCTGC-3') (SEQ ID NO:30) were used. To determine whether the transformants carry correct insertions, primers oSM61-GUS-N (5'-TCACACCGATACCATCAGCG-3') (SEQ ID NO:29) and oSK138-petA-3'-re (5'-AATCGTAACCAGTC TCTACTGG-3') (SEQ ID NO:31) were used. The PCR program used was as follows: 3 min at 94° C., 1 cycle; 45 sec at 94° C., 45 sec at 55° C., 2 min at 72° C., 30 cycles; final extension at 72° C. for 10 min.

For detection of the aph-6 gene and the nptII gene specific primers were used. To determine whether the transformants carry correct insertions one gene specific primer and primer oSK138-petA-3'-re are used.

Southern blotting analysis are carried out as described in example 1 and in standard protocols.

Example 5

Selection for Paraquat Tolerance

Plant Transformation and Selection for Paraquat Resistance 4 leaf pieces were transformed each with 1 μg pIC558 (FIG. 8) as described in example 4. After bombardment the leaf pieces were incubated for 2 days at 25° C. on RMOP-medium.

Two days after bombardment leaves were cut into small pieces (ca. 3×3 mm), transferred to fresh RMOP-medium and incubated for 10 days in the dark at 25° C. Then leaf pieces were cut again, transferred to fresh medium containing 5 mg/l paraquat and incubated for 10 days in the light at 25° C. The leaf pieces were cut again, transferred to fresh medium containing 8 mg/l paraquat and incubated for 12 days in the light at 25° C. Green regenerates from the bottom side were retrieved and transferred to individual plates containing RMOP with 8 mg/l paraquat. The lines were subjected to repeated cycles of shoot generation by cutting small leaf pieces, which form new regenerates on RMOP-medium with 8 mg/l paraquat.

Molecular Analysis of Potential Plastid Transformants by Southern Analysis 3 mg of total plant DNA per analysed plant are digested with the appropriate restriction enzyme and separated on a TBE-agarose gel (1%). The DNA is denatured and transferred to a positively charged nylon membrane (Hybond-N+, Amersham) as described in Ausubel et al., 1999: Short protocols in molecular biology, Wiley, 4$^{th}$ edition, Unit 2.9A. The filter is hybridised with digoxigenin-labelled probes in DIG Easy Hyb Buffer (Roche Diagnostics GmbH, Mannheim, Germany), and hybridisation signals are detected using the DIG Luminescent Detection Kit (Roche). The membrane is exposed to a X-OMAT LS film at room temperature.

A fragment suitable for discrimination between wild type and transformed plastome is gel purified using the QIAquick Gel Extraction Kit (QIAgen, Hilden, Germany), labelled with digoxigenin using the Roche DIG DNA Labelling Kit and used for hybridisation.

Example 6

Reconstitution of ycf3 Using Kanamycin Selection

Construction of Transformation Vector pIC577 for Targeted Inactivation of the ycf3 Gene A transformation vector was constructed designed to inactivate the ycf3 gene by replacing the first exon and the splicing site of ycf3 (corresponding to plastome nucleotides 46042–46206) with the aadA coding region. This vector does not contain any 3' regulatory elements (neither for the aadA marker gene, nor for the endogenous ycf3 or tRNA gene). In addition, no promoter elements were introduced, and the aadA gene is expected to be transcribed and translated by the endogenous ycf3 upstream regulatory element.

This vector contains the aadA coding region, flanked by 5'- and 3'-homologous sequences which were amplified from the tobacco chloroplast genome by PCR using the following two pairs of primers: oFCH76 (5'-Nco I-GTA GCA ATC CAT TCT AGA AT-3', (SEQ ID NO:22), annealing with plastome nucleotides 46269–46288) and oFCH77 (5'-Sma I-CGG AAA GAG AGG GAT TCT AAC-3', (SEQ ID NO:32), annealing with plastome nucleotides 47205–46185); oFCH78 (5'-Sph I-GAA GTT TCT TTC TTT GCT ACA-3' (SEQ ID NO:33), annealing with plastome nucleotides 45033–45053) and oFCH79 (5'-Pst I-TAC GCT TTT T GA AGG TGA AGT-3' (SEQ ID NO:34), annealing with plastome nucleotides 46041–46021).

The PCR amplification using Pfu polymerase (Promega) was performed as follows: 2 min at 94° C., 1 cycle; 45 sec at 94° C., 45 sec at 55° C., 2 min at 72° C., 30 cycles; final extention at 72° C. for 10 min. The amplified 5'-homologous fragment (corresponding to plastome nucleotides 46269–47205), containing 936 nucleotides upstream of the ycf3 start codon, was digested with Sma I and Nco I and then ligated into pUC16SaadA plasmid (Koop et al., 1996) which was digested with Eco RI, followed by a fill-in reaction using Klenow polymerase (Promega) and then digested with Nco I, generating pIC565. The amplified 3'-homologous fragment (corresponding to plastome nucleotides 45033–46041), containing 1000 nucleotides of the ycf3 gene, was digested with Pst I and Sph I, and then ligated into pIC565 cut with Pst I and Sph I, yielding the final transformation vector pIC577 (FIGS. 12 and 13). The identity of the plasmid insert was verified by sequencing (MWG, Munich).

Primary Transformation and Selection of Homoplastomic Δycf3 Mutants

Young leaves from sterile tobacco plants (cultivation see example 3) were bombarded with plasmid pIC577-coated gold particles using the Bio-Rad (Hercules, Calif., USA) PDS1000/He Biolistic particle delivery system (detailed procedure see example 3). Two days after bombardment, leaves were cut into small pieces (ca. 3×3 mm) and transferred to solid RMOP-medium containing 500 µg/ml spectinomycin. Leaf pieces were cut again and transferred to fresh medium after 2 weeks, then every 3 weeks until no further regenerants appeared. Primary Δycf3 transformants displayed spectinomycin-resistance and a green phenotype in the light while still being heteroplastomic. In order to amplify transformed plastid DNA molecules and to eliminate wild-type genomes, the primary transformants were subjected to 3 additional rounds of regeneration on selective medium. Since segregation leads to the occurrence of white and green sectors, material from white sectors was subjected to several additional rounds of regeneration on non-selective medium in order to obtain homoplastomic mutant transformants. Homoplastomic transformed lines were rooted and propagated on solid VBW-medium (Aviv and Galun, 1985; see example 3).

Analysis by PCR and Southern Blotting

Plastid transformants were identified by PCR amplification. The total DNA isolated from the first regenerates of 24 independent lines were used as a template for PCR. Two sets of primers (the sequences see example 3): oFCH59 and oFCH60; oFCH52 and oFCH53 were employed to analyze transplastomic plants. oFCH52 and oFCH53 should result in an amplification product of 900 bp from the wild-type plastome and a product of 1476 bp from transformed plastomes, whereas oFCH59 and oFCH60 should result in an amplification product of 480 bp from the transformed plants and no product from wild-type. The results show that 14 lines of transformants carry correct aadA insertions in the plastid genome. The data are also consistent with phenotypic appearance of the respective lines, which indicated that the pigment deficiency was correlated with deletion of ycf3.

Homoplasmy was verified by DNA gel blot analysis. Genomic DNAs isolated from young leaves of Δycf3 mutants (4$^{th}$ regenerates) grown under low light conditions were used for DNA gel blot analysis. Detailed procedure was as follows: 4 µg of total plant DNA per analyzed plant was digested with restriction enzyme Xma JI and separated on a TAE-agarosegel (0.8%). The DNA was denatured and transferred to a positively charged nylon membrane (Hybond-N$^+$, Amersham) as described in Ausubel et al. (1999). The filter was hybridized with digoxigenin-labeled probes in DIG Easy Hyb Buffer (Roche Diagnostics GmbH, Mannheim, Germany), and hybridization signals were detected using the DIG Luminescent Detection Kit (Roche). The membrane was exposed to a X-OMAT LS film at room temperature for 2 hours.

For preparation of a DIG-labeled probe, tobacco genomic DNA was used as template to amplify a 520 bp fragment using the following pair of primers: oFCH69 (5'-CAT TGG AAC TGC TAT GTA GGC-3' (SEQ ID NO:17), corresponding to tobacco plastome sequence 47149–47169) and oFCH64 (5'-GAA TTA CCA AAC CAT TTG ACC C-3' (SEQ ID NO:13),corresponding to tobacco plastome sequence 47667–47647). The PCR DIG Probe Synthesis Kit from Roche was used. The PCR program was as follows: 2 min at 94° C., 1 cycle; 30 sec at 94° C., 30 sec at 55° C., 1 min at 72° C., 30 cycles; final extension at 72° C. for 10 min. The amplified fragment was gel purified using the QIAquick Gel Extraction Kit Qiagen, Hilden, Germany) and then used for hybridization. This probe should result in a signal of 2780 bp from the transformed plastomes and a signal of 2198 bp from wild-type plastomes. The result showed that no wild-type plastid DNA could be detected in all 6 examined mutant lines.

Construction of the Transformation Vector pIC637 for Reconstitution of the ycf3 Gene Transformation vector pIC637 was designed to transform the mutant Δycf3 line with the goal to reconstitute the ycf3 gene, delete the aadA gene and insert the aphA-6 gene that confers resistance to kanamycin at the same time.

The aphA-6 gene is introduced into the upstream position of ycf3 without disruption of either ycf3 expression or the function of the endogenous ycf3 upstream regulatory element. A short RBS (ribosomal bonding site) sequence serves as the signal to translate the reconstituted ycf3 gene as a newly formed artificial operon. The aphA-6 gene and ycf3 are transcribed in the same direction under control of ycf3 5'-regulatory element.

The region of the tobacco chloroplast genome (corresponding to plastome nucleotides 45033–46266) containing the N-terminal of ycf3 (which is deleted in the first round transformation) was amplified from genomic DNA isolated from leaf tissue of tobacco by PCR. The following pair of oligonucleotide primers were used: oFCH139 (5'-Pst I-ATC ACT AGT TGT AGG GAG GGA TCC (ribosome binding site)-ATG CCT AGA TCA CGG ATA AA-3' (SEQ ID NO:35), annealing with plastome nucleotides 46266–46247) and oFCH78 (5'-Sph I-GAA GTT TCT TTC TTT GCT ACA-3' (SEQ ID NO:33), annealing with plastome nucleotides 45033–45053). The PCR amplification using Taq polymerase (Promega) was performed as follows: 2 min at 94° C. 1 cycle; 45 sec at 94° C., 45 sec at 55° C., 2 min at 72° C., 30 cycles; final extension at 72° C. for 10 min. The fragment was digested with Pst I and Sph I, and then ligated into pIC577 cut with Pst I and Sph I, generating pIC636.

The coding region of the aphA-6 gene was cut from the plasmid pSK.KmR (obtained from Dr. Saul Purton, Department of Biology University college London, UK) using Nco I and Pst I and then ligated into pIC636 cut with Nco I and Pst I, yielding the final transformation vector pIC637 (FIGS. 14 and 15). The identity of the plasmid insert was verified by sequencing (MWG, Munich).

Plastid Transformation of Δycf3 Mutant Lines and Selection of Homoplastomic Lines The goal of the second transformation was to reconstitute the ycf3 gene, remove the aadA marker and introduce the aphA-6 gene that confers resistance to kanamycin at the same time. Embedded protoplasts isolated from sterile homoplastomic Δycf3 mutants grown under low light conditions on solid VBW-medium were bombarded with plasmid pIC637-coated gold particles using the Bio-Rad (Hercules, Calif., USA) PDS-1000/He Biolistic particle delivery system (detailed procedure see example 3). Two days after bombardment, grids were transferred to solid RMOP medium, containing 25 µg/ml kanamycin and cultivated under low light conditions for two weeks. Afterwards, every two weeks grids were transferred to fresh medium and cultivated under strong light conditions until no further regenerates appeared. The transformants which display kanamycin resistance and a green phenotype were selected and subjected to B5 medium under strong light condition to amplify ycf3-reconstituted plastomes (ycf3-deficient plastomes can not be amplified when growing on B5 medium and strong light conditions).

Molecular Analysis of the Secondary Transplastomic Plants

Plastid transformants were identified by PCR amplification. The total DNA isolated from primary transformants which displayed green phenotype and were able to grow photoautotrophically was used as a template for PCR analysis using the following two pairs of primers: oFCH168 (5'-TCA GTC GCC ATC GGA TGT TT-3' (SEQ ID NO:36), derived from the 5' portion of the aphA-6 coding region) and oFCH169 (5'-ACC AAT CTT TCT TCA ACA CG-3' (SEQ ID NO:37), derived from the 3' portion of the aphA-6 coding region); oFCH27 (5'-TGC TCA AGA CTT TAG TGG ATC-3' (SEQ ID NO:16), annealing with plastome nucleotides 44799–44819) and oFCH168. oFCH168 and oFCH169 should result in an amplification product of 500 bp from the reconstituted plants and no product from unchanged first round transformants. The combination of oFCH27 and oFCH168 can determine whether the second round transformants carry correct aphA-6 insertions or not by amplifying a product of about 2300 bp from correctly transformed plastomes. In total, 5 unique ycf3-reconstituted tobacco plastid transformants were obtained from 3 grid bombardments.

Homoplasmy was verified by DNA gel blot analysis. Genomic DNA was isolated from young leaves of ycf3-reconstituted plants grown on B5 medium under strong light conditions and digested with Hinc II. The probe used was the same as that for Δycf3 mutants (detailed procedures for DNA blotting and hybridization see above). The probe generates a signal of 3257 bp for wild-type plastome, a signal of 2046 bp for plastomes correctly transformed in the second round, and a signal of 3857 bp for unchanged first round transformants.

To confirm the removal of the aadA marker a second hybridization of the blot (of which the former probe had been removed by a stripping procedure) was done using a 480 bp fragment of the aadA-gene as probe. For probe generation primers oFCH59 and oFCH60 (see above) were used in a PCR DIG labeling reaction according to the protocol of the supplier (Roche).

REFERENCES

Allison L A, Simon L D, Maliga P 1996, EMBO J. 15: 2802–2809.

Ausubel (ed.), Current Protocols in Molecular Biology, John Wiley and Sons, Inc. (1999).

Ausubel et al., 1999: Short protocols in molecular biology, Wiley, 4th edition.

Aviv, D and Galun, E 1985, J. Hered. 76: 135–136.

Bock R, Kössel H, Maliga P 1994, EMBO J. 13:4623–8.

Boynton J. E., Gillham N. W., Harris E. H., Hosler J. P., Johnson A. M., Jones A. R., Randolph-Anderson B. L., Robertson D., Klein T. M., Shark K. B., et al. (1988), Science, 240, 1534–1538.

Carrer H., Hockenberry T. N., Svab Z., Maliga P. 1993, Mol Gen Genet 241: 49–56.

Daniell H., Datta R., Varma S., Gray S., Lee S. B., 1998, Nat. Biotech., 16, 345–348.

De Santis-Maclossek G, Kofer W, Bock A, Schoch S, Maier R M, Wanner G, Rüdiger W, Koop H U, Herrmann R G 1999, Plant J. 18:477–89.

Dovzhenko A, Bergen U, Koop H U 1998, Protoplasma 204, 114–18.

Eibl C, Zou Z, Beck a, Kim M, Mullet J, Koop H U 1999, Plant J., 19, 333–345.

Fischer N, Stampacchia O, Redding K, and Rochaix J D, 1996, Mol Gen Genet 251, 373–380.

Galvin S. B., 1998, Curr. Opin. Biotechnol., 9, 227–232.

Goldschmidt-Clermont (1991) Nucl Acids Res 19, 4083–4089.

Gray M. W., Origin and Evolution of Plastid Genomes and Genes, in: Bogorad L. and Vasil I. K. (eds.), Cell Culture and Somatic Cell Genetics of Plants, Volume 7A, Academic Press, San Diego, 1991.

Heifetz, 2000, Biochimie, 82, 655–666.

Hock and Elstner, 1995: Schadwirkung auf Pflanzen; Spektrum, 3. Auflage; pages 155–186

Iamtham, S, Day, A., 2000, Nature Biotechnology 18, 1172–1176.

Kavanagh T. A., Thanh N. D., Lao N. T., McGrath N., Peter S. O., Horvath E. M., Dix P. J., Medgyesy P., 1999, Genetics, 152, 1111–1122.

Khan M S, Maliga P, Nat Biotechnol 1999, 17:910–5.

Koop H U, Steinmüller K, Wagner H, Rössler C, Eibl C, Sacher L 1996, Planta, 199: 193–201.

Krause K, Maier R M, Kofer W, Krupinska K, Herrmann R G 2000, Mol. Gen. Genet. 263: 1022–1030.

Maniatis, E. F. Fritsch and J. Sambrook, Molecular Cloning: A Laboratory Manual, Cold Spring Harbor laboratory, Cold Spring Harbor, N.Y. (1989).

Marechal-Drouard L., Kuntz M., Weil J. H., tRNAs and tRNA Genes of Plastids, in: Bogorad L. and Vasil I. K. (eds.), Cell Culture and Somatic Cell Genetics of Plants, Volume 7 A, Academic Press, San Diego, 1991.

Monde R A, Greene J C, Stern D B 2000 Mol Gen Genet 263(4):610–8.

Monde R A, Zito F, Olive J, Wollman F A, Stern 2000 Plant J:61–72.

Palmer J. D., Plastid Chromosomes: Structure and Evolution, in: Bogorad L. and Vasil I. K. (eds.), Cell Culture and Somatic Cell Genetics of Plants, Volume 7A, Academic Press, San Diego, 1991.

Ruf S, Kössel H, Bock R1997, J. Cell Biol. 139: 95–102.

Silhavy, M. L. Berman, and L. W. Enquist, Experiments with Gene Fusions, Cold Spring Harbor Laboratory, Cold Spring Harbor, N.Y. (1984).

Svab Z, Hajdukiewicz, P, Maliga P 1990, Proc Natl Acad Sci USA 87:8526–8530.

Svab Z. & Maliga P., 1993, Proc. Natl. Acad. Sci. USA 90, 913–917.

The Arabidopsis Genome Initiative, 2000, Nature 408: 796–815.

The invention claimed is:

1. A process for producing a multicellular dicotyledonous plant, plant organ or plant tissue having a transformed plastome, wherein the plant, plant organ or plant tissue is selected from the group consisting of potato, tomato and tobacco, the process comprising the following steps:
   (a) altering or disrupting the function of a gene in a plastid genome for producing a selectable or recognizable phenotype, wherein said phenotype is a pigment deficiency and/or photosynthesis deficiency;
   (b) separating or selecting a plant, plant organ or plant tissue having plastids expressing said phenotype from plants, plant organs or plant tissues having plastids that do not express said phenotype, thereby producing a separated or selected plant, plant organ or plant tissue having plastids expressing said phenotype;
   (c) transforming said plastid genome of said separated or selected plant, plant organ or plant tissue expressing said phenotype with at least one transformation vector having a restoring sequence capable of restoring said function; and
   (d) separating or selecting said transformed plant, plant organ or plant tissue having plastids expressing said restored function from non-transformed plant, plant organ or plant tissue which does not express said restored function.

2. The process according to claim 1, wherein the transformation of step (c) restores said function in conjunction with introducing at least one additional function.

3. The process according to claim 1, wherein the transformation of step (c) restores said function in conjunction with causing a desired additional genetic modification of the plastid genome.

4. The process according to claim 1, wherein the transformation of step (c) additionally eliminates a preexisting function in another gene in said plastid genome of said separated or selected plant, plant organ or plant tissue.

5. The process according to claim 1, wherein said alteration or disruption of step (a) is obtained by induced mutation.

6. The process according to claim 1, wherein said alteration or disruption of step (a) is obtained by genetic transformation.

7. The process according to claim 6, wherein said genetic transformation results simultaneously in the introduction of at least one additional sequence for at least one additional function.

8. The process according to claim 7, wherein said additional function is an inhibitor resistance function and step (b) is carried out in the presence of the corresponding inhibitor.

9. The process according to claim 8, wherein the inhibitor present in step (b) is not present during regeneration.

10. The process according to claim 1, wherein step (a) alters or disrupts a trophic type and step (c) restores a trophic type.

11. The process according to claim 10, wherein the restored trophic type is phototrophy.

12. The process according to claim 1, wherein step (c) restores a deficiency produced in step (a).

13. The process according to claim 1, wherein the altering or disrupting of gene function in step (a) is done using a vector, further wherein the vector(s) used in step (a) and/or or (c) comprise(s) a sequence having homology to a host plastid sequence sufficient for homologous recombination.

14. The process according to claim 1, wherein the plant, plant organ, or plant tissue in step (b) is grown or cultured in a medium supporting heterotrophic growth.

15. The process according to claim 1, wherein said alteration or disruption of step (a) produces a pigment deficient phenotype.

16. The process according to claim 15, wherein said pigment deficient phenotype is chlorophyll deficiency.

17. The process according to claim 1, wherein the gene function altered or disrupted in step (a) is the function of a plastome encoded plastid gene essential for transcription or translation.

18. The process according to claim 1, wherein the gene function altered or disrupted in step (a) is the function of a plastid rpoA or rpoB gene.

19. The process according to claim 1, wherein the phenotype produced in step (a) can alternate between two or several appearances dependent on external growth conditions.

20. The process according to claim 19, wherein the gene function altered or disrupted in step (a) is the function of a plastid ycf3 gene, producing a yellow-white phenotype under standard light conditions and a light green phenotype under low light conditions.

21. The process according to claim 1, wherein the gene function altered or disrupted in step (a) is the function of a plastid gene which produces a high chlorophyll fluorescence phenotype upon alteration or disruption, preferably petA.

22. The process according to claim 21, wherein the separation or selection in step (b) utilizes an inhibitor that requires active photosynthesis for efficacy.

23. The process according to claim 22, wherein said inhibitor is paraquat, morphamquat, diquat, difenzoquat and/or cyperquat.

24. The process according to claim 1, wherein photomixotrophic conditions are used in step (d).

25. The process according to claim 1, wherein the altering or disrupting of gene function in step (a) and the restoring of said gene function in step (c) comprises the introduction of a sequence in step (a) and the introduction of a sequence in step (c), further wherein the sequence introduced in step (a) and the sequence introduced in step (c) together result in an additional function.

26. The process according to claim 1, wherein the separating or selecting of said plant, plant organ or plant tissue in step (d) further comprises separating or selecting a plant, plant organ or plant tissue exhibiting resistance to an inhibitor from a plant, plant organ or plant tissue which does not exhibit resistance to the inhibitor.

27. The process according to claim 1, wherein the gene function altered or disrupted in step (a) is the function of a plastid psbA gene.

* * * * *

UNITED STATES PATENT AND TRADEMARK OFFICE
CERTIFICATE OF CORRECTION

PATENT NO. : 7,193,131 B2
APPLICATION NO. : 10/466221
DATED : March 20, 2007
INVENTOR(S) : Eibl et al.

It is certified that error appears in the above-identified patent and that said Letters Patent is hereby corrected as shown below:

Column 5,
Line 50: Correct "plastid/c II" to read --plastid/cell--

Line 51: Correct "ins rtion sit" to read --insertion site--

Line 52: Correct "interg nic region" to read --intergenic region--

Column 7,
Line 4: Correct "ribos mal binding" to read --ribosomal binding--

Column 24,
Line 4: Correct "Kit Qiggen, Hilden, Germany)"
        To read --Kit (Qiagen, Hilden, Germany)--

Column 30,
Line 28: Correct "Kit Qiagen, Hilden, Germany)"
        To read --Kit (Qiagen, Hilden, Germany)--

Signed and Sealed this

Twenty-fifth Day of September, 2007

JON W. DUDAS
*Director of the United States Patent and Trademark Office*